US012692560B2

(12) United States Patent
Durandet et al.

(10) Patent No.: US 12,692,560 B2
(45) Date of Patent: Jul. 28, 2026

(54) PATHOGEN DETECTION IN LIQUID MATRIX

(71) Applicant: INGÉNIERIE ET ANALYSE EN GÉNÉTIQUE ENVIRONNEMENTALE, Montpellier (FR)

(72) Inventors: Franz Durandet, Montferrier sur Lez (FR); Élodie Pichon, Montpellier (FR); Jawhar Saksaka, Montpellier (FR); Olivier Couillerot, Assas (FR)

(73) Assignee: INGÉNIERIE ET ANALYSE EN GÉNÉTIQUE ENVIRONNEMENTALE, Montpellier (FR)

( * ) Notice: Subject to any disclaimer, the term of this patent is extended or adjusted under 35 U.S.C. 154(b) by 514 days.

(21) Appl. No.: 18/260,181

(22) PCT Filed: Dec. 30, 2021

(86) PCT No.: PCT/EP2021/087880
§ 371 (c)(1),
(2) Date: Jun. 30, 2023

(87) PCT Pub. No.: WO2022/144432
PCT Pub. Date: Jul. 7, 2022

(65) Prior Publication Data
US 2024/0060147 A1 Feb. 22, 2024

(30) Foreign Application Priority Data
Dec. 31, 2020 (EP) .................................... 20306715

(51) Int. Cl.
| | | |
|---|---|---|
| *C12Q 1/70* | (2006.01) | |
| *C12Q 1/00* | (2006.01) | |
| *C12Q 1/6804* | (2018.01) | |
| *C12Q 1/6806* | (2018.01) | |
| *C12Q 1/6851* | (2018.01) | |
| *C12Q 1/689* | (2018.01) | |

(52) U.S. Cl.
CPC ........... *C12Q 1/701* (2013.01); *C12Q 1/6851* (2013.01); *C12Q 1/689* (2013.01); *C12Q 1/6806* (2013.01); *C12Q 2600/16* (2013.01)

(58) Field of Classification Search
CPC ....... G01N 2333/165; G01N 33/56983; C12Q 2600/16; C12Q 1/6806; C12Q 1/6851
See application file for complete search history.

(56) References Cited

U.S. PATENT DOCUMENTS

2003/0050470 A1* 3/2003 An ........................ C07H 21/00
435/6.14

FOREIGN PATENT DOCUMENTS

| CN | 110144364 | * | 8/2019 |
|---|---|---|---|
| CN | 111286558 | * | 6/2020 |

OTHER PUBLICATIONS

International Search Report and Written Opinion issued on Apr. 14, 2022, in corresponding International Application No. PCT/EP2021/087880, 10 pages.
Peccia et al., "Measurement of SARS-CoV-2 RNA in wastewater tracks community infection dynamics", Nature Biotechnology, Gale Group Inc, New York, vol. 38, No. 10, Sep. 18, 2020, 10 pages.
Harb et al., "Molecular-based detection of potentially pathogenic bacteria in membrane bioreactor (MBR) systems treating municipal wastewater: a case study", Environmental Science and Pollution Research International, Ecomed, Landsberg, DE, vol. 24, No. 6, Dec. 24, 2016, 11 pages.
Kitamura et al., "Efficient detection of SARS-CoV-2 RNA in the solid fraction of wastewater", Science of the Total Environment, Elsevier, Amsterdam, NL, vol. 763, Dec. 18, 2020, 7 pages.
D'Aoust et al., "Quantitative analysis of SARS-CoV-2 RNA from wastewater solids in communities with low COVID-19 incidence and prevalence", Water Research, Elsevier, Amsterdam, NL, vol. 188, Oct. 23, 2020,13 pages.
Racki et al., "One-step RT-droplet digital PCR: a breakthrough in the quantification of waterborne RNA viruses", Analytical and Bioanalytical Chemistry, vol. 406, No. 3, Nov. 26, 2013, 7 pages.

* cited by examiner

*Primary Examiner* — Barry A Chestnut

(74) *Attorney, Agent, or Firm* — Maier & Maier, PLLC

(57) ABSTRACT

Methods, reagents and a kit for the detection of a pathogen in a test sample, notably a sample of an environmental water matrix. The method involves the detection by multiplex digital PCR (dPCR) of several pathogen sequences without prior purification of the sample. Also, a method for detection of the Severe Acute Respiratory Syndrome Coronavirus 2 (SARS-CoV-2) virus in a sample, notably sample of an environmental water matrix.

19 Claims, 4 Drawing Sheets

Specification includes a Sequence Listing.

SEQUENCE LISTING

<160> NUMBER OF SEQ ID NOS: 30

<210> SEQ ID NO 1
<211> LENGTH: 24
<212> TYPE: DNA
<213> ORGANISM: Artificial
<220> FEATURE:
<223> OTHER INFORMATION: probe

<400> SEQUENCE: 1
accccgcatt acgtttggtg gacc                                          24

<210> SEQ ID NO 2
<211> LENGTH: 23
<212> TYPE: DNA
<213> ORGANISM: Artificial
<220> FEATURE:
<223> OTHER INFORMATION: probe -continued

<400> SEQUENCE: 2
acaatttgcc cccagcgctt cag                                             23

<210> SEQ ID NO 3
<211> LENGTH: 26
<212> TYPE: DNA
<213> ORGANISM: Artificial
<220> FEATURE:
<223> OTHER INFORMATION: probe

<400> SEQUENCE: 3
acactagcca tccttactgc gcttcg                                          26

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gaccccaaaa tcagcgaaat                                                 20

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
tctggttact gccagttgaa tctg                                            24

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ttacaaacat tggccgcaaa                                                 20

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
gcgcgacatt ccgaagaa                                                   18

<210> SEQ ID NO 8
<211> LENGTH: 26
<212> TYPE: DNA
<213> ORGANISM: Artificial
<220> FEATURE:
<223> OTHER INFORMATION: primer

<400> SEQUENCE: 8
acaggtacgt taatagttaa tagcgt                                          26

<210> SEQ ID NO 9
<211> LENGTH: 22

```
<212> TYPE: DNA
<213> ORGANISM: Artificial
<220> FEATURE:
<223> OTHER INFORMATION: primer

<400> SEQUENCE: 9
atattgcagc agtacgcaca ca                                              22

<210> SEQ ID NO 10
<211> LENGTH: 16
<212> TYPE: DNA
<213> ORGANISM: Artificial
<220> FEATURE:
<223> OTHER INFORMATION: probe

<400> SEQUENCE: 10
cctaccgaag caaatg                                                     16

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gagtggtttg accttaacgt ttga                                           24

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ttgtcggttg caatgcaagt                                                20

<210> SEQ ID NO 13
<211> LENGTH: 25
<212> TYPE: DNA
<213> ORGANISM: Artificial
<220> FEATURE:
<223> OTHER INFORMATION: Forward primer Enterococcus durans

<400> SEQUENCE: 13
ttatgtccca gtattgaaaa atcaa                                          25

<210> SEQ ID NO 14
<211> LENGTH: 23
<212> TYPE: DNA
<213> ORGANISM: Artificial
<220> FEATURE:
<223> OTHER INFORMATION: Reverse primer  Enterococcus durans

<400> SEQUENCE: 14
gtgaatcata ttggtatgca gtc                                            23

<210> SEQ ID NO 15
<211> LENGTH: 18
<212> TYPE: DNA
<213> ORGANISM: Artificial
<220> FEATURE:
<223> OTHER INFORMATION: Forward primer Hepatitis A virus

<400> SEQUENCE: 15
```

-continued tcaccgccgt ttgcctag                                                        18

<210> SEQ ID NO 16
<211> LENGTH: 19
<212> TYPE: DNA
<213> ORGANISM: Artificial
<220> FEATURE:
<223> OTHER INFORMATION: Reverse primer  Hepatitis A virus

<400> SEQUENCE: 16
ggagagccct ggaagaaag                                                       19

<210> SEQ ID NO 17
<211> LENGTH: 20
<212> TYPE: DNA
<213> ORGANISM: Artificial
<220> FEATURE:
<223> OTHER INFORMATION: Forward primer Escherichia coli spp

<400> SEQUENCE: 17
ccagtttgcg ttcaataccg                                                      20

<210> SEQ ID NO 18
<211> LENGTH: 20
<212> TYPE: DNA
<213> ORGANISM: Artificial
<220> FEATURE:
<223> OTHER INFORMATION: Reverse primer Escherichia coli spp

<400> SEQUENCE: 18
gtcgctagaa aacgtccgta                                                      20

<210> SEQ ID NO 19
<211> LENGTH: 17
<212> TYPE: DNA
<213> ORGANISM: Artificial
<220> FEATURE:
<223> OTHER INFORMATION: Forward primer Norovirus GI

<400> SEQUENCE: 19
gctggatgcg cttccat                                                         17

<210> SEQ ID NO 20
<211> LENGTH: 23
<212> TYPE: DNA
<213> ORGANISM: Artificial
<220> FEATURE:
<223> OTHER INFORMATION: Reverse primer Norovirus GI

<400> SEQUENCE: 20
ccttagacgc catcatcatt tac                                                  23

<210> SEQ ID NO 21
<211> LENGTH: 26
<212> TYPE: DNA
<213> ORGANISM: Artificial
<220> FEATURE:
<223> OTHER INFORMATION: Forward primer Norovirus GII

<400> SEQUENCE: 21
atgttcagat ggatgagatt ctcaga                                               26

<210> SEQ ID NO 22
<211> LENGTH: 21
<212> TYPE: DNA
<213> ORGANISM: Artificial

-continued

```
<220> FEATURE:
<223> OTHER INFORMATION: Reverse primer Norovirus GII

<400> SEQUENCE: 22
tcgacgccat cttcattcac a                                          21

<210> SEQ ID NO 23
<211> LENGTH: 21
<212> TYPE: DNA
<213> ORGANISM: Artificial
<220> FEATURE:
<223> OTHER INFORMATION: Forward primer Candida albicans

<400> SEQUENCE: 23
ttggtatttt gcatgttgct c                                          21

<210> SEQ ID NO 24
<211> LENGTH: 21
<212> TYPE: DNA
<213> ORGANISM: Artificial
<220> FEATURE:
<223> OTHER INFORMATION: Reverse primer Candida albicans

<400> SEQUENCE: 24
gtcagaggct ataacacaca g                                          21

<210> SEQ ID NO 25
<211> LENGTH: 28
<212> TYPE: DNA
<213> ORGANISM: Artificial
<220> FEATURE:
<223> OTHER INFORMATION: Probe Enterococcus durans

<400> SEQUENCE: 25
cgtagggatc tccaaagcgg aaaatcgg                                   28

<210> SEQ ID NO 26
<211> LENGTH: 20
<212> TYPE: DNA
<213> ORGANISM: Artificial
<220> FEATURE:
<223> OTHER INFORMATION: Probe Hepatitis A virus

<400> SEQUENCE: 26
cctgaacctg caggaattaa                                            20

<210> SEQ ID NO 27
<211> LENGTH: 24
<212> TYPE: DNA
<213> ORGANISM: Artificial
<220> FEATURE:
<223> OTHER INFORMATION: Probe Escherichia coli spp

<400> SEQUENCE: 27
cctgccgcgt tggcaatgtc gagt                                       24

<210> SEQ ID NO 28
<211> LENGTH: 29
<212> TYPE: DNA
<213> ORGANISM: Artificial
<220> FEATURE:
<223> OTHER INFORMATION: Probe Norovirus GI

<400> SEQUENCE: 28
cggattgtgg acaggagatc gcgatcttc                                  29
```

-continued

```
<210> SEQ ID NO 29
<211> LENGTH: 22
<212> TYPE: DNA
<213> ORGANISM: Artificial
<220> FEATURE:
<223> OTHER INFORMATION: Probe Norovirus GII

<400> SEQUENCE: 29
gagcacgtgg gagggcgatc gc                                                        22

<210> SEQ ID NO 30
<211> LENGTH: 22
<212> TYPE: DNA
<213> ORGANISM: Artificial
<220> FEATURE:
<223> OTHER INFORMATION: Probe Candida albicans

<400> SEQUENCE: 30
tttaccgggc cagcatcggt tt                                                        22
```

PATHOGEN DETECTION IN LIQUID MATRIX

FIELD

The present invention provides methods, reagents and a kit for the detection of a pathogen in a test sample, notably a sample of an environmental water matrix. The method involves the detection by multiplex digital PCR (dPCR) of several pathogen sequences without prior purification of the sample. In one embodiment, the invention provides a method for detection of the Severe Acute Respiratory Syndrome Coronavirus 2 (SARS-CoV-2) virus in a sample, notably sample of an environmental water matrix.

Other virus, bacteria and fungi are also illustrated with the method of the invention.

BACKGROUND

Water is essential to life. An adequate, safe and accessible supply must be available to all. Improving access to safe drinking-water can result in significant benefits to health. According to the WHO Drinking water key facts of 2018, contaminated drinking water is the cause of diarrhoeal deaths estimated to be at 502,000 per to drinking water year. 844 million people lack access service, and 423 million utilise well and spring water with 159 million still dependent on untreated surface water from lakes, ponds, rivers, and streams.

Water quality control remains an important topic of public health since some diseases, such as diarrhoea, hepatitis, and cholera, are caused by its consumption. It is well known that the greatest microbial risks are associated with ingestion of water that is contaminated with human or animal faeces. Wastewater discharges in fresh waters and costal seawaters are the major source of faecal microorganisms, including pathogens. Drinking water thus can contain bacteria, protozoa, and viruses that can cause a variety of diseases in humans, most notably gastroenteritis. Although consumption of contaminated drinking-water represents the greatest risk, other routes of transmission can also lead to disease, with some pathogens transmitted by multiple routes (e.g., adenovirus). Certain serious illnesses, such as legionellosis, caused by *Legionella* spp., result from inhalation of water droplets carrying the causative microorganism. The microbiological quality control of water for human consumption thus requires a simple and reliable assessment of the presence of pathogens.

Tracking microorganisms in water sources is also useful for other purposes, since it has been shown that viruses can be detected in human feces before the onset of symptoms in the local population (Medema et al. 2020, Lesimple et al. 2020). Wastewater-Based Epidemiology (WBE) is thus a new epidemiology approach that postulates that through the analysis of population pooled wastewater, infectious disease and resistance spread, the emergence of new disease outbreak to the community level can be monitored comprehensively and in real-time (Hart, & Halden, 2020, *Sci Total Environ.* 730:138875). Various microorganisms, notably pathogens such as *Escherichia coli* or the SARS-CoV-2 virus, are indeed present in wastewater. Monitoring sewage for traces of a pathogen thus enables effective surveillance of entire communities, providing a sensitive signal of whether the pathogen is present in the population and whether transmission is increasing or declining. Determination of the length of time these pathogens can persist in wastewater or a wastewater-impacted environment (e.g., potable water source, bathing water, irrigation water, food crop), as well as faecal wastes, biosolids, and soil is essential when assessing the potential public health impact associated with use of that water or food crop. It is also a critical factor when examining treatment in faecal waste treatment, lagoons, wetlands and other land-based methods (Yates, M. 2017. Persistence of Pathogens in Sewage and Other Water Types. In: J. B. Rose and B. Jiménez-Cisneros, (eds) Global Water Pathogen Project. www.waterpathogens.org (M. Yates (eds) Part 4 Management of Risk from Excreta and Wastewater) www.waterpathogens.org, E. Lansing, MI, UNESCO; Murphy, Heather. (2018). Persistence of Pathogens in Sewage and Other Water Types. 10.14321/waterpathogens.51.).

Techniques such as the Polymerase Chain Reaction (PCR) allow direct detection of the pathogen genetic material and, in theory, can detect the presence of trace amounts of pathogen nucleic acids. For example the presence of SARS-CoV-2 in sewage was detected by reverse transcription-quantitative polymerase chain reaction (RT-qPCR) and surveillance of relative changes in concentrations of SARS-CoV-2 RNA at the inlet of wastewater treatment plant over time was suggested to serve as a useful tool for early warning for virus spread in the population (Medema et al., 2020, *Environ Sci Technol Lett.* 20:511-516; Randazzo et al., 2020, *Water Res.* 181:115942; Peccia et al., 2020, *Nat. Biotechnol.* 38:1164-1167; Trottier et al., 2020, *One Health.* 10:100157; Wurtzer et al., 2020, *Euro Surveill.* 25 (50): pii=2000776).

A fundamental limiting factor in the assessment of microbial quality of waters is often the very low number of each organism present. Therefore, it is important to note that the methods of pathogen detection in water require a high degree of sensitivity, which is unfortunately not afforded by the present methods. In addition, monitoring methods are needed to quantify with accuracy both the abundance and the expression levels of the pathogen genes. Thus there is still a need for more sensitive and efficient methods of detecting pathogens in water.

SUMMARY

The present invention relates to a method of detecting a pathogen in an environmental water matrix sample. This method involves the detection of several pathogen sequences by multiplex digital PCR (dPCR).

The present method is particularly advantageous since it does not require sample purification before the pathogen nucleic acid is extracted from the sample and used as a template in the multiplex dPCR reaction. In comparison, methods of the prior art required some degree of purification of the sample in order to eliminate any PCR-inhibitory substances that are initially present in the matrix. For example, CDC recommendations for SARS-CoV-2 wastewater detection studies include a step of clarifying the sample before the viral RNA is extracted (www.cdc.gov). This step is generally thought to be required to remove inhibitors preventing amplification of nucleic acids from the sample (see e.g., Ahmed et al., 2020, *Sci Total Environ.* 739:139960). The inventors showed that, surprisingly and contrary to this commonly-held belief in the art, omission of the initial purification step leads to higher nucleic acid recovery without significantly hampering downstream amplification by dPCR, thereby enabling the detection of lower pathogen concentrations in the environmental water matrix. Indeed, as low as 200 copies/L can be detected by the present method for a coronavirus (SARS-CoV-2), while the theoretical detection limit of the methods of the prior art can be estimated to be at least 10 times higher (see e.g., Ahmed et al., 2020, J Travel Med. 27 (5): taaa116. doi: 10.1093/jtm/taaa116; Graham et al., 2020, *Environ Sci Technol*. acs.est.0c06191. doi: 10.1021/acs.est.0c06191; Wu et al., 2020; mSystems. 5 (4): e00614-20.). For example, considering a medium wastewater generation rate and a medium SARS-CoV-2 virus excretion rate mentioned in the data of Hart et al 2020, the present method should be able to detect an infected person within a wastewater sample representing 100.000 persons, instead of 1 infected person in 2.000 people (Hart, & Halden, 2020, *Sci Total Environ*. 730: 138875). The present method is thus more sensitive than those of the prior art.

DETAILED DESCRIPTION

Figure 1:
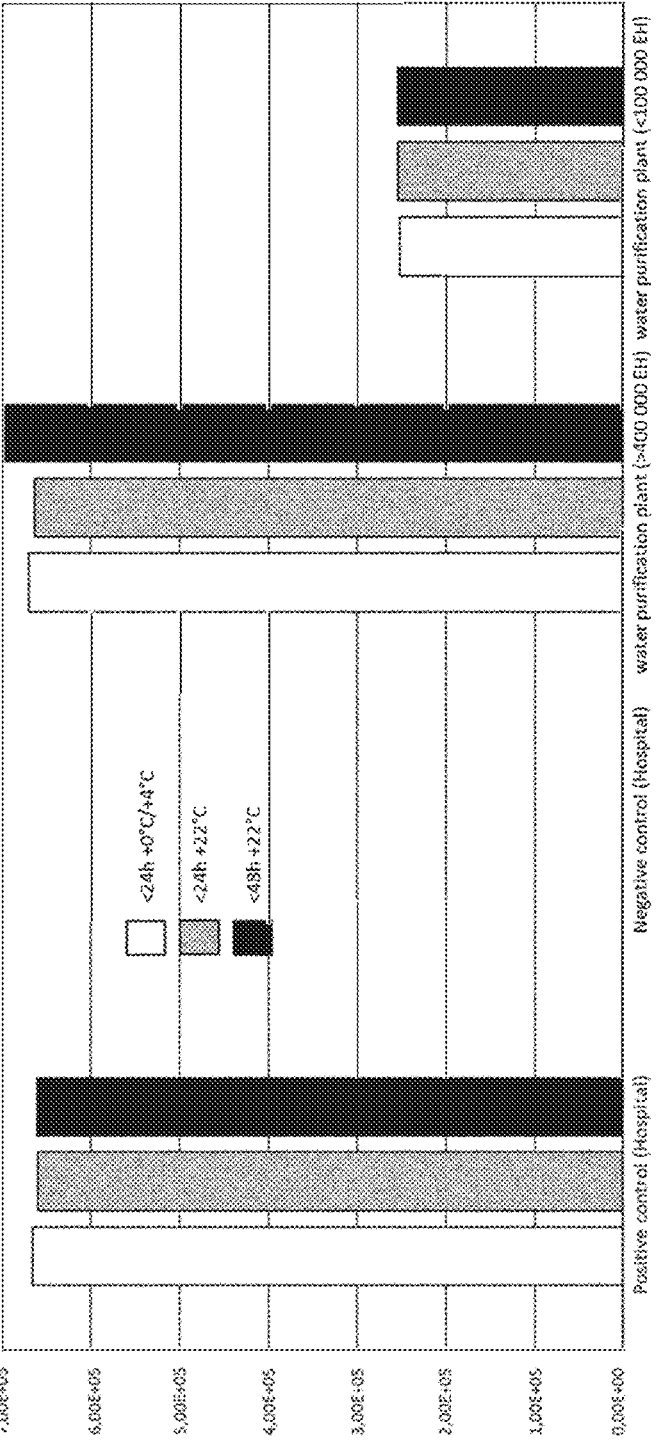
FIG. 1: Evaluation of the storage temperature on the yield of the method.

In a first aspect, the present disclosure relates to a method of detecting a pathogen in an environmental liquid matrix, comprising:

a) taking a sample of environmental water matrix, and b) extracting nucleic acid without previous purification of the sample, and c) amplifying at least 2 pathogen sequences in a multiplex digital PCR (dPCR) reaction using the nucleic acid of step b) as a template.

The method described herein allows for the detection of any pathogen present in an environmental water matrix. A "pathogen" as used herein is an organism associated with, or causative of, a disease or condition of plants or animals. Non-limiting examples of pathogens may include viruses inclusive of RNA and DNA viruses, protozoa, fungi, worms inclusive of helminths, roundworms and annelids and bacteria inclusive of Gram+ and Gram bacteria. Preferably, the pathogens that can be detected with the present method are viruses or bacteria. Such pathogens can be of any origin. They can infect any type of host. Notably, they can be human or zoonotic. They may be found naturally in water, as part of their life cycle. Detection of such pathogens may help decide whether a water matrix is safe. In another aspect, these pathogens are only detectable in water when there is an infection.

Thus, any pathogen which can be present in a water sample can be detected by the present method. Notably the method described herein can be used for detecting the presence of bacteria, viruses, and/or fungi in a water sample. Bacteria that can be detected by the present method include e.g., *Salmonella* spp., *Yersinia* spp., including *Y. pestis, Y. pseudotuberculosis*, and *Y. enterocolitica, Listeria monocytogenes, Taylorella equigenitalis, Mycoplasma* gallisepticum/*Mycoplasma* synoviae, *Trichinella* spp., *Toxoplasma gondii*, Mastitis causing bacteria, such as e.g., *Escherichia coli, Streptococcus uberis, Staphylococcus aureus*, and other Gram-positive and catalase-negative cocci, and *Legionella*, notably *L. pneumophila*. Alternatively, bacteria that can be detected by the present method are selected in the group consisting of: *Salmonella* spp., *Yersinia* spp., including *Y. pestis, Y. pseudotuberculosis*, and *Y. enterocolitica, Listeria monocytogenes, Taylorella equigenitalis, Mycoplasma gallisepticum/Mycoplasma synoviae, Trichinella* spp., *Toxoplasma gondii*, Mastitis causing bacteria, such as e.g., *Escherichia coli, Streptococcus uberis, Staphylococcus aureus*, and other Gram-positive and catalase-negative cocci, and *Legionella*, notably *L. pneumophila*. Viruses that can be detected by the method described herein include adenoviruses, astroviruses, hepatitis A and E viruses, rotavirus, norovirus and other caliciviruses, enteroviruses, including coxsackieviruses and polioviruses, polyomaviruses, cytomegalovirus, influenza viruses, including human and zoonotic viruses, notably influenza A virus (e.g. human, avian, or swine influenza A virus), coronaviruses, including porcine epidemic diarrhoea virus, SARS-CoV1, SARS-CoV-2, and MERS Cov, Paramyxoviridae, notably of the Morbillivirus genus (e.g., rinderpest virus), bluetongue virus (BTV), bovine viral diarrhoea virus (BVDV), Schmallenberg virus, classical swine fever virus (CSFV), Betaarterivirus suid 1 (formerly Porcine reproductive and respiratory syndrome virus or PRRSV), and African Swine Fever Virus. In another aspect, viruses that can be detected by the method described herein are selected in the group consisting of: adenoviruses, astroviruses, hepatitis A and E viruses, rotavirus, norovirus and other caliciviruses, enteroviruses, including coxsackieviruses and polioviruses, polyomaviruses, cytomegalovirus, influenza viruses, including human and zoonotic viruses, notably influenza A virus (e.g., human, avian, or swine influenza A virus), coronaviruses, including porcine epidemic diarrhoea virus, SARS-CoV1, SARS-CoV-2, and MERS Cov, Paramyxoviridae, notably of the Morbillivirus genus (e.g., rinderpest virus), bluetongue virus (BTV), bovine viral diarrhoea virus (BVDV), Schmallenberg virus, classical swine fever virus (CSFV), Betaarterivirus suid 1 (formerly Porcine reproductive and respiratory syndrome virus or PRRSV), and African Swine Fever Virus. Fungi that can be detected by the present method include *Candida albicans, Cryptococcus neoformans, Aspergillus fumigatus, Aspergillus niger, Trichophyton* spp, *Fusarium, Scedosporium, Alternaria, Exophiala, Histoplasma, Coccidioides*, and *Penicillium marneffei*, and mixtures thereof.

Preferably, the pathogen detected in the present method is a coronavirus. More preferably, it is SARS-CoV-2.

In another particular embodiment, the pathogen detected in the present method is a norovirus.

In another particular embodiment, the pathogen detected in the present method is hepatitis A virus.

In another particular embodiment, the pathogen detected in the present method is a bacteria, such as *Enterococcus durans* or *Escherichia coli*, preferably *Escherichia coli*.

In another particular embodiment, the pathogen detected in the present method is a fungus, in particular *Candida albicans*.

An "environmental water matrix" as used herein, refers to a water source which is susceptible to contain the pathogen to be tested. Such water sources include inter alia ground water, precipitation (rain or snow), surface water (lakes, ponds, river, runoff, etc.), ice or glacial melt, saline water, estuarian water and brines, waste water (domestic, landfill leachates, mine runoff, etc.), industrial process water and drinking water. Preferably, the environmental water matrix is selected in the group consisting of ground water, precipitation (rain or snow), surface water (lakes, ponds, river, runoff, etc.), ice or glacial melt, saline water, estuarian water and brines, waste water (domestic, landfill leachates, mine runoff, etc.), industrial process water and drinking water.

Samples of the environmental water matrix may be taken in accordance with any suitable process known to the person of skills in the art (see e.g., Madrid et al., 2007, *Trends in Analytical Chemistry*, 26(4): 293-299). Guidelines of water sampling have notably been published by various governmental agencies (see e.g., www.env.go.jp).
In particular, the sampling process will depend upon the environmental water matrix.

The sample of step a) may represent a single collection of water from the environmental water matrix. Alternatively, this sample may be obtained by pooling various samples collected from the environmental water matrix. In an aspect, at least 2, at least 3, at least 4, at least 5, at least 10, at least 20 samples of water are pooled to constitute the sample of step a) of the present method.

Those various samples may be taken all at once or over an extended period of time. For example, they may be taken over at least 1 hour, 2 hours, 3 hours, 4 hours, 5 hours, 6 hours, 12 hours, 18 hours, 24 hours, or 48 hours. Alternatively, they may be taken over 1 hour, 2 hours, 3 hours, 4 hours, 5 hours, 6 hours, 12 hours, 18 hours, 24 hours, or 48 hours. Preferably, the samples are taken over 24 hours.

The volume of the sample is preferably comprised between 100 mL and 1 L.

Preferably, the sample is kept at a temperature comprised between 1° C. and 4° C. between step a) and step b) of the method described herein. Alternatively, the sample is kept at a temperature above 4° C., preferably at ambient temperature, more preferably at a temperature between 20° C. and 25° C., even more preferably at 21° C. between step a) and step b) of the method described herein. Indeed, the inventors have shown that, contrary to a commonly-held belief in the art (see e.g., www.cdc.gov), the samples can be kept 48 hours at a temperature above 4° C. (notably at 21° C.) without any significant decrease in the assay sensitivity.

Environmental water matrix samples are usually not homogeneous and contain colloidal or suspended particulates. It is thought that this may interfere with nucleic acid recovery and subsequent PCR analysis, as interferences can bias estimated concentrations of nucleic acid target sequences (see e.g., EPA, EPA 821-R-19-003: Method 1697: Characterization of Human Fecal Pollution in Water by HumM2TaqMan® Quantitative Polymerase Chain Reaction (qPCR) Assay®, March 2019). Methods of the prior art thus comprise a first purification step whose purpose is to remove cells and other large debris, thereby yielding a homogenous liquid sample. Notably, methods of the prior art comprise a clarification step. By "clarification", it is herein referred to the process of separating any colloidal or particulate material from the water phase. Clarification is commonly performed by any means available to the person of skill in the art, such as e.g., passing the sample through large pore size filters, preferably 5 μm or larger, or centrifuging the sample, preferably at a centrifugal force comprised between 4,000×g and 5,000×g, more preferably at 4,654×g (see e.g., CDC recommendations for SARS-CoV-2 wastewater detection studies; Medema et al., 2020, *Environ Sci Technol Lett.* 20:511-516).

The present inventors have found that this clarification step leads to a loss of genetic material, thereby preventing the detection of very low levels of nucleic acid of the pathogen present in the sample. In fact, comparison data show consistently higher levels of recovered pathogen nucleic acid (e.g., SARS-Cov-2 RNA) when the clarification step is omitted. Moreover, the efficiency of the multiplex dPCR step is not affected by the absence of a clarification step. Accordingly, the present method does not comprise a clarification step prior to RNA extraction.

Advantageously, the sample may be homogenised before RNA extraction. Preferably, the sample is homogenised by thorough mixing. Alternatively, homogenising may involve vortexing the sample. More preferably, an homogenous sample is obtained by thorough mixing and vortexing of the sample. Without being bound by theory, this step is thought to detach the pathogen, notably viral particles such as SARS-CoV-2 viral particles from the colloidal or particulate materials present in the sample.

In another aspect, the method described herein may comprise a step of concentrating the sample. Preferably, this step of concentrating the sample takes place after step a). Preferably, this step of concentrating the sample takes place after step a) and after the sample has been homogenised as described above. Advantageously, the sample is concentrated by contacting the sample with a filter, e.g., a centrifugal filter. Preferably, the filter has a cutoff of 10 kDa, i.e., molecules having a molecular weight below 10 kDa are separated from the sample by the further step. The present inventors have found that using filters with higher cutoffs (e.g., 100 kDa; see e.g., Medema et al., 2020, *Environ Sci Technol Lett.* 20:511-516) leads to a reduction of the amount of pathogen nucleic acid (e.g., SARS-CoV-2 RNA) recovered and thus to a diminution of the method sensitivity. Using a centrifugal filter is advantageous because concentration can be easily achieved by centrifuging the sample contacted with the centrifugal filter and recovering the supernatant. For example, the supernatant volume may be less than 2 mL, preferably less than 1 mL, more preferably less than 500 μL.

In a particular aspect, the filter (e.g., a centrifugal filter) may be contacted with water prior to being contacted with the sample. The water used in this step is advantageously purified water such as e.g., distilled or mili-Q or ultrapurified water. In addition, it may be particularly advantageous to use a water which is DNase-free and/or RNase-free. Preferably, the water is at a temperature comprised between 60° C. and 80° C., preferably at a temperature comprised between 65° C. and 75° C., more preferably at a temperature of 70° C. Moreover, it may advantageous to centrifuge the filter contacted with the water before contacting this filter with the sample.

The amplification steps according to the method described herein can be performed with any nucleic acid from the pathogen. A nucleic acid is a nucleotide polymer. As used herein "nucleic acid" or "polynucleotide" refers interchangeably to nucleotide polymers composed of deoxyribonucleotides, ribonucleotides, or a mixture of both. The nucleic acid may comprise modified nucleotides. Modified nucleotides include nucleotides that have been labelled with a detectable moiety, such as a fluorescent or radioactive group. The skilled person will realise immediately that the nucleic acid used in the present method is dictated by the pathogen of interest. For example, the genetic material of bacteria is usually DNA. Likewise, some viruses contain DNA, which may be either single-stranded or double-stranded (e.g., adenovirus, cytomegalovirus, polyomavirus, etc.). Other viruses contain RNA, either single-stranded (e.g., coronaviruses, hepatitis A and E viruses, influenza viruses, etc.) or double-stranded (e.g., bluetongue virus, rotaviruses). Preferably, the nucleic acid used in the method above is desoxyribonucleic acid (DNA). More preferably, the nucleic acid is genomic DNA. Alternatively, the nucleic acid is ribonucleic acid (RNA).

The nucleic acids used in the method described herein may be extracted from the pathogen or may be synthesised chemically using well known techniques in the art. Most preferably, said nucleic acid is extracted from the pathogen of interest by any method which is known by the person of skills in the art for this purpose. In preferred embodiments, the nucleic acid is isolated or purified after the extraction of step b).

For the purposes of this invention, by "isolated" or "purified" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical, synthetic or recombinant form. "Isolated" or "purified" notably refers in relation to a nucleic acid to a nucleotide polymer in the form of a separate fragment or as a component of a larger nucleic acid construct, which has been derived from nucleic acid isolated from its natural environment at least once. An "isolated nucleic acid" refers to a nucleic acid segment or fragment, which has been separated from sequences, which flank it in a naturally occurring state, e.g., a DNA fragment that has been removed from the sequences, which are normally adjacent to the fragment, e.g., the sequences adjacent to the fragment in a genome in which it naturally occurs.

In other preferred aspects, the nucleic acid which is used as template in any of the amplification reaction is purified from the other pathogen components. Accordingly, the term "isolated nucleic acid" also applies to nucleic acids, which have been substantially purified, from other components, which naturally accompany the nucleic acid, e.g., RNA or DNA, or proteins, which naturally accompany it in the cell. Such pathogen nucleic acid template may be prepared by a mere lysis of the bacterial cell wall or the viral envelope by any method known in the art. For example, nucleic acids can be extracted using liquid extraction (e.g., Trizol, DNAzol) techniques. Nucleic acids can also be extracted using commercially available kits (e.g., NucleoSpin RNA Virus, QIAamp Circulating Nucleic Acid Kit, Qiagen DNeasy kit, QIAamp kit, Qiagen Midi kit, QIAprep spin kit). Kits are available commercially for extracting DNA or RNA from bacteria or viruses (see e.g., Becker et al., 2016, *Sci Rep.* 6:28063; Zhang et al., 2018, *BMC Genomics.* 19:773; Burgener et al., 2003, *J Virol Methods.* 108 (2): 165-170; Sathiamoorthy et al., 2018, *npj Vaccines.* 3:31). Nucleic acids can be concentrated or precipitated by known methods, including, by way of example only, centrifugation. Nucleic acids can be bound to a selective membrane (e.g., silica) for the purposes of purification. Nucleic acids can also be enriched for fragments of a desired length, e.g., fragments which are less than 1000, 500, 400, 300, 200 or 100 base pairs in length. Such an enrichment based on size can be performed using, e.g., PEG-induced precipitation, an electrophoretic gel or chromatography material (Huber et al., 1993, *Nucleic Acids Res.* 21:1061-6), gel filtration chromatography, or TSKgel (Kato et al., 1984, *J. Biochem,* 95:83-86), which publications are hereby incorporated by reference in their entireties for all purposes.

The nucleic acid extraction of step b) typically yields a solution comprising the isolated pathogen nucleic acid and a buffer, and optionally salts. This solution, or partition thereof, is then used in step c) to amplify the desired target sequences.

As used herein, "amplify", "amplifying" or "amplification reaction" and their derivatives, refer generally to any action or process whereby at least a portion of a nucleic acid molecule (referred to as a template nucleic acid molecule) is replicated or copied through a template-dependent in vitro enzyme-catalysed reaction into at least one additional nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule.

One method which is commonly used for amplifying genetic material is the polymerase chain reaction (PCR). The PCR process is well known in the art (U.S. Pat. Nos. 4,683,195, 4,683,202 and 4,800,159). In PCR, nucleic acid primers that are complementary to opposite strands of a nucleic acid amplification target sequence are permitted to anneal to the denatured sample. Next, DNA polymerase (typically heat stable) extends the DNA duplex from the hybridised primer. The process is then repeated to amplify the nucleic acid target. If the nucleic acid primers do not hybridise to the sample, then there is no corresponding amplified PCR product. In this case, the PCR primer acts as a hybridisation probe. Preferably, the PCR technique used quantitatively measures starting amounts of DNA, cDNA, or RNA. Examples of PCR-based techniques include techniques such as, but not limited to, quantitative PCR (Q-PCR), reverse-transcriptase polymerase chain reaction (RT-PCR), quantitative reverse-transcriptase PCR (QRT-PCR), or digital PCR (dPCR). These techniques are well known and easily available technologies for those skilled in the art and do not need a precise description.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available. Improved and more sensitive PCR methods such as real-time PCR and digital PCR are also useful in certain embodiments of the present invention.

Preferably, the amplification of the pathogen nucleic acid is performed by digital PCR. The term "digital polymerase chain reaction" or "digital PCR" or dPCR" as used herein refers to a refined version of conventional polymerase chain reaction (PCR) methods that can be used to directly quantify and clonally amplify nucleic acids including DNA, cDNA or RNA, such that the amount of target nucleic acid can be directly quantitatively measured. Digital PCR achieves this direct quantitative measurement by capturing or isolating each individual nucleic acid molecule present in a sample within many separate reaction chambers that are able to localise and concentrate the amplification product to detectable levels. Digital PCR involves multiple PCR analyses on extremely dilute nucleic acids such that most positive amplifications reflect the signal from a single template molecule: in a digital assay, the sample is first diluted and partitioned into small containers such that each partition contains a discrete number of biological entities. Digital PCR thereby permits the counting of individual template molecules. After PCR amplification, a count of chambers containing the PCR end-product is a direct measure of the absolute nucleic acid quantity. Each partition is then individually assayed, giving a 0 or 1 result if any molecules are present.

The capture or isolation of individual nucleic acid molecules, typically by way of dilution, may be effected in capillaries, microemulsions, arrays of miniaturised chambers, or on nucleic acid binding surfaces. The basic methodology of dPCR is described in, e.g., Sykes et al., Biotechniques 13 (3): 444-449, 1992; Vogelstein et al., *Proc Natl Acad Sci USA* 96:9236-924, 1999; Quan et al., 218, Sensors (Basel). 18 (4): 1271; and The dMIQE Group and Huggett, 2020, *Clin Chem.* 66 (8): 1012-1029. Numerous devices for performing dPCR are available commercially, including BioMark dPCR from Fluidigm, QuantStudio12k flex dPCR, 3D dPCR from Life Technologies, QX100 and QX200 from Bio-Rad, RainDrop from RainDance, Naica System from Stilla, and QIAcuity from Qiagen.

Since template molecule quantification by dPCR does not rely on dose-response relationships between reporter dyes and nucleic acid concentrations, its analytical precision is, therefore, superior to that of real-time PCR. Hence, dPCR has the sensitivity to register extremely minute quantities of viral genetic material and distinguish it from complex mixtures. In the present case, the inventors have found dPCR to be essential to detect very low amounts of pathogen nucleic acid (DNA or RNA) in a sample of an environmental water matrix.

In a preferred aspect of the method described herein, the pathogen nucleic acid is quantified in the sample of the environmental liquid matrix based on the amplification by multiplex dPCR of step c). Accordingly, the present disclosure also relates to a method of detecting a pathogen in an environmental liquid matrix, comprising:

a) taking a sample of the environmental liquid matrix, and b) extracting nucleic acid without prior purification of the sample, notably without prior clarification of the sample, c) amplifying at least 2 pathogen sequences in a multiplex digital PCR (dPCR) reaction using the nucleic acid of step b) as a template, and d) quantifying the nucleic acid in the sample of the environmental liquid matrix based on the amplification of step c).

Quantifying the nucleic acid is advantageous since it allows easy comparison between different samples. For example, quantifying by the method described herein the copies of the SARS-CoV-2 (or other viruses, bacteria, fungi as illustrated in the examples) present at different times in the same water source, e.g., a wastewater source, is useful for monitoring an infection by this virus in a human population.

Preparation of the nucleic acid solution for the dPCR assay may include any suitable manipulation of the nucleic acid, such as collection, dilution, concentration, purification, lyophilisation, freezing, extraction, combination with one or more assay reagents, performance of at least one preliminary reaction to prepare the nucleic acid for one or more reactions in the assay, or any combination thereof, among others. Preparation of the nucleic acid solution may include rendering the nucleic acid solution competent for subsequent performance of one or more reactions, such as one or more enzyme catalysed reactions and/or binding reactions.

As with all other PCR formats, dPCR is preferably performed with a DNA substrate. Accordingly, RNA transcripts may first be converted to complementary DNA (cDNA) in reverse transcriptase digital PCR (RT-dPCR). In a one-step strategy, RNA is partitioned with both reverse transcription and PCR occurring sequentially in the same partition. In two-step reactions, reverse transcription is first performed in bulk before partitioning the cDNA and subsequent dPCR in a separate reaction.

In some embodiments, preparation of the nucleic acid solution may include combining the nucleic acid solution with reagents for amplification and for reporting whether or not amplification occurred. Reagents for amplification may include any combination of primers for the targets, dNTPs and/or NTPs, at least one enzyme (e.g., a polymerase, a ligase, a reverse transcriptase, a restriction enzyme, or a combination thereof, each of which may or may not be heat-stable), and/or the like. Accordingly, preparation of the nucleic acid may render the nucleic acid solution (or partitions thereof) capable of amplification of each of one or more targets, if present, in the nucleic acid solution (or a partition thereof). Reagents for reporting may include a different reporter for each target of interest. Accordingly, preparation of the nucleic acid solution for reporting may render the nucleic acid solution capable of reporting, or being analysed for, whether or not amplification has occurred, on a target-by-target basis, and optionally the extent of any such amplification. The reporters each may be a labelled probe that includes a nucleic acid (e.g., an oligonucleotide) labelled with a luminophore (i.e., a photoluminescent moiety), such as a fluorophore.

The nucleic acid solution may be separated into partitions. Separation of the nucleic acid solution may involve distributing any suitable portion or all of the sample to the partitions. Each partition may be and/or include a fluid volume that is isolated from the fluid volumes of other partitions. Partitioning is preferably accomplished using two general approaches: (1) arrays of physically isolated chambers or wells or (2) droplet emulsions where the reaction is conducted in water droplets separated by a continuous oil phase. The partitions may thus be isolated from one another by a carrier fluid, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 μL, less than about 100, 10, or 1 nL, or less than about 100, 10, or 1 μL, among others. The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like. Any of the reagents may be combined with the partitions (or a bulk phase sample) in a macrofluidic or microfluidic environment.

In one embodiment, the PCR solution may be partitioned by use of e.g., a digital PCR system, including a fluid input, a fluid output, a set of microfluidic channels, and at least one heating element. In such examples, the set of microfluidic channels fluidly connect the fluid input and the fluid output. Preferably, each microfluidic channel of the set comprises a reaction chamber. At least one heating element is positioned in each reaction chamber. The at least one heating element may heat fluid in the reaction chamber of each fluid channel.

Furthermore, the at least one heating element may pump fluid to the reaction chamber and pump fluid from the reaction chamber of each microfluidic channel. Example devices described herein may be used to perform a PCR process by electrically actuating a heating element in a reaction chamber to cause at least one reaction of the PCR process.

In some aspects, the sample holder may have a plurality of sample regions, or wells, configured for receiving a plurality of samples, wherein the wells may be sealed within the sample holder via a lid, cap, sealing film or any other sealing mechanism between the wells and heated cover. Some examples of a sample holder may include, but are not limited to, any size multi-well plate, card or array including, but not limited to, a 24-well microtiter plate, 48-well microtiter plate, a 96-well microtiter plate, a 384-well microtiter plate, a microcard, a through-hole array, or a substantially planar holder, such as a glass or plastic slide. The wells in various embodiments of a sample holder may include depressions, indentations, ridges, and combinations thereof, patterned in regular or irregular arrays formed on the surface of the sample holder substrate. Sample or reaction volumes can also be located within wells or indentations formed in a substrate, spots of solution distributed on the surface a substrate, or other types of reaction chambers or formats, such as samples or solutions located within test sites or volumes of a microfluidic system, or within or on small beads or spheres.

In some instances, a PCR solution may be pumped to a reaction chamber of each microfluidic channel with the at least one heating element. The PCR solution in the reaction chamber may be heated for amplification of a DNA template included in the PCR solution with the at least one heating element, and the PCR solution may be pumped from the reaction chamber of each microfluidic channel with the at least one heating element. Notably, the device may heat fluid to various temperatures for operations corresponding to a polymerase chain reaction process.

In an embodiment of dPCR, the PCR solution may be divided into smaller reactions through for example a water oil emulsion technique, which are then made to run PCR individually. The PCR sample can be partitioned into nano-liter-size samples and encapsulated into oil droplets. The oil droplets are made using a droplet generator that applies a vacuum to each of the wells. Approximately 20,000 oil droplets are made from each 20 μL sample.

Droplets can be generated having an average diameter of about 0.001, 0.01, 0.05, 0.1, 1, 5, 10, 20, 30, 40, 50, 60, 70, 80, 100, 120, 130, 140, 150, 160, 180, 200, 300, 400, or 500 microns. The average diameter of the droplets can be about 0.001 microns to about 0.01 microns, about 0.001 microns to about 0.005 microns, about 0.001 microns to about 0.1 microns, about 0.001 microns to about 1 micron, about 0.001 microns to about 10 microns, about 0.001 microns to about 100 microns, about 0.001 microns to about 500 microns, about 0.01 microns to about 0.1 microns, about 0.01 microns to about 1 micron, about 0.01 microns to about 10 microns, about 0.01 microns to about 100 microns, about 0.01 microns to about 500 microns, about 0.1 microns to about 1 micron, about 0.1 microns to about 10 microns, about 0.1 microns to about 100 microns, about 0.1 microns to about 500 microns, about 1 micron to about 10 microns, about 1 micron to about 100 microns, 1 micron to about 500 microns, about 10 microns to about 100 microns, about 10 microns to about 500 microns, or about 100 microns to about 500 microns.

Droplet volume can be about, more than about, less than about, or at least about 0.001 nL, 0.01 nL, 0.1 nL, 1 nL, 10 nL, or 100 nL. Alternatively, droplet volume can be at least about 0.001 nL, 0.01 nL, 0.1 nL, 1 nL, 10 nL, or 100 nL. Alternatively, droplet volume can be less than about 0.001 nL, 0.01 nL, 0.1 nL, 1 nL, 10 nL, or 100 nL. Droplets can be generated using, e.g., RAINSTORM™ (RAIN-DANCE™), microfluidics from ADVANCED LIQUID LOGIC, or ddPCR™ (BIO-RAD). Microfluidic methods of producing emulsion droplets using microchannel cross-flow focusing or physical agitation can produce either monodisperse or polydisperse emulsions. The droplets can be monodisperse droplets. The droplets can be generated such that the size of said droplets does not vary by more than plus or minus 5% of the average size of said droplets. The droplets can be generated such that the size of said droplets does not vary by more than plus or minus 2% of the average size of said droplets. A droplet generator can generate a population of droplets from a single sample, wherein none of the droplets can vary in size by more than plus or minus 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Both the flow rate in a droplet generator and the length of nucleic acids in a sample can have an impact on droplet generation. One way to decrease extension is to decrease flow rate; however, this can have the undesirable side effect of lower throughput and also increased droplet size. Long nucleic acids can disrupt droplet formation in extreme cases, resulting in a steady flow rather than discrete droplets. Reducing nucleic acid size in a sample can improve droplet formation when nucleic acid loads are high. Samples with high nucleic acid loads (e.g., high DNA loads, high RNA loads, etc.) can be used. Reducing the length of nucleic acids in a sample (e.g., by digestion, sonication, heat treatment, or shearing) can improve droplet formation.

Higher mechanical stability can be useful for microfluidic manipulations and higher-shear fluidic processing (e.g., in microfluidic capillaries or through 90 degree turns, such as valves, in a fluidic path). Pre- and post-thermally treated droplets or capsules can be mechanically stable to standard pipette manipulations and centrifugation.

A droplet can be formed by flowing an oil phase through an aqueous sample. A droplet can comprise a buffered solution and reagents for performing an amplification reaction, e.g., a PCR reaction, including nucleotides, primers, probe(s) for fluorescent detection, template nucleic acids, DNA polymerase enzyme, and/or reverse transcriptase enzyme.

A partition can comprise a buffered solution and reagents for performing an enzymatic reaction (e.g., a PCR). The buffered solution can comprise about 1, 5, 10, 15, 20, 30, 50, 100, or 200 mM Tris. A partition can comprise one or more buffers including, e.g., TAPS, bicine, Tris, Tricine, TAPSO, HEPES, TES, MOPS, PIPES, cacodylate, SSC, ADA, ACES, cholamine chloride, acetamidoglycine, glycinamide, maleate, phosphate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, methylamine, or MES. The pH of the partition can be about 2, 2.5, 3, 3.5, 4, 4.5, 5, 5.5, 6, 6.5, 6.6, 6.7, 6.8, 6.9, 7, 7.1, 7.2, 7.3, 7.4, 7.5, 7.5, 7.6, 7.7, 7.8, 7.9, 8, 8.1, 8.2, 8.3, 8.4, 8.5, 8.6, 8.7, 8.8, 8.9, 9, 9.5, 10, 10.5, 11, 11.5, 12, or 12.5. The pH of the partition can be about 5 to about 9, about 5 to about 8, about 5 to about 7, about 6.5 to about 8, about 6.5 to about 7.5, about 6 to about 7, about 6 to about 9, or about 6 to about 8.

A partition can comprise a salt, e.g., potassium acetate, potassium chloride, magnesium acetate, magnesium chloride, sodium acetate, or sodium chloride. The concentration of potassium chloride can be about 10, 20, 30, 40, 50, 60, 80, 100, 200 mM. The buffered solution can comprise about 15 mM Tris and about 50 mM KCl.

A partition can comprise nucleotides. The nucleotides can comprise deoxyribonucleotide triphosphate molecules, including dATP, dCTP, dGTP, dTTP, in concentrations of about, more than about, less than about, or at least about 50, 100, 200, 300, 400, 500, 600, or 700 μM each. dUTP can be added within a partition, e.g., an aqueous phase of an emulsion, to a concentration of about 50, 100, 200, 300, 400, 500, 600, 700, 800, 900, or 1000 μM. The ratio of dUTP to dTTP in a partition can be about 1:1000, 1:500, 1:250, 1:100, 1:75, 1:50, 1:40, 1:30, 1:20, 1:10, 1:5, 1:4, 1:3, 1:2, or 1:1.

A partition can comprise one or more divalent cations. The one or more divalent cations can be, e.g., $Mg^{2+}$, $Mn^{2+}$, $Cu^{2+}$, $Co^{2+}$, or $Zn^{2+}$. Magnesium chloride ($MgCl_2$) can be added to a partition at a concentration of about 1.0, 2.0, 3.0, 4.0, or 5.0 mM. The concentration of $MgCl_2$ can be about 3.2 mM.

Magnesium sulfate can be substituted for magnesium chloride, at similar concentrations. A partition can comprise both magnesium chloride and magnesium sulfate. A wide range of common, commercial PCR buffers from varied vendors can be substituted for the buffered solution.

A non-ionic ethylene oxide/propylene oxide block copolymer can be added to a partition in a concentration of about 0.1%, 0.2%, 0.3%, 0.4%, 0.5%, 0.6%, 0.7%, 0.8%, 0.9%, or 1.0%. A partition can comprise a biosurfactant. Common biosurfactants include non-ionic surfactants such as Pluronic F-68, Tetronics, Zonyl FSN. Pluronic F-68 can be present at a concentration of about 0.5% w/v.

A partition can comprise one or more additives including, but not limited to, non-specific background/blocking nucleic acids (e.g., salmon sperm DNA), biopreservatives (e.g., sodium azide), PCR enhancers (e.g., betaine (N,N,N-trimethylglycine; [carboxymethyl]trimethylammonium), trehalose, etc.), and/or inhibitors (e.g., RNAse inhibitors). A GC-rich additive comprising, e.g., betaine and DMSO, can be added to samples assayed in the methods provided herein. The one or more additives can include a non-specific blocking agent such as BSA or gelatine from bovine skin. The gelatine or BSA can be present in a concentration range of approximately 0.1 to about 0.9% w/v. Other blocking agents can include betalactoglobulin, casein, dry milk, or other common blocking agents. In some cases, the concentration of BSA and gelatine are about 0.1% w/v. The one or more additives include can 2-pyrrolidone, acetamide, N-methylpyrolidone (MP), B-hydroxyethylpyrrolidone (HEP), propionamide, NN-dimethylacetamide (DMA), N-methylformamide (MMP), NN-dimethylformamide (DMF), formamide, N-methylacetamide (MMA), polyethylene glycol, tetramethylammonium chloride (TMAC), 7-deaza-2'-deoxyguanosine, T4 gene 32 protein, glycerol, or nonionic detergent (Triton X-100, Tween 20, Nonidet P-40 (P-40), Tween 40, SDS (e.g., about 0.1% SDS)), salmon sperm DNA, sodium azide, formamide, dithiothreitol (DTT), beta-mercaptoethanol (BME), 2-mercaptoethylamine-HCl, tris (2-carboxythyl)phosphine (TCEP), cysteine-HCl, or a plant polysaccharide. The one or more additives can be ethanol, ethylene glycol, dimethylacetamide, dimethylformamide, or suphalane.

Each partition may contain a probe or a plurality of probes that hybridise to amplicons produced in the partitions. A "probe" as used herein refers to a nucleic acid connected to at least one label. As used herein, a "label" is an identifying and/or distinguishing marker or identifier connected to or incorporated into any entity, such as a compound, biological particle (e.g., a cell, bacteria, spore, virus, or organelle), or partition. A label may, for example, be a dye that renders an entity optically detectable and/or optically distinguishable. Exemplary dyes used for labelling are fluorescent dyes (fluorophores) and fluorescence quenchers. A probe may be a sequence-specific binding partner for a nucleic acid target and/or amplicon. Preferably, the partition contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes. In one instance, the amplification of the target sequence comprises the use of at least one probe capable of binding to at least one target sequence.

In a PCR method, the amplified nucleic acid product may be detected in a number of ways. Several fluorescence-based detection methods can be performed in real-time and comprise using a probe which hybridises to the amplification products. Examples of such fluorescence-based methods include the adjacent hybridisation probes (Wittwer, C T. et al., 1997, BioTechniques 22:130-138), molecular beacon probes (Tyagi S. and Kramer F. R. 1996, Nat. Biotech. 14:303-308) and scorpion probes (Whitcomb et al., 1999, Nat. Biotech. 17:804-807). Adjacent hybridisation probes are usually designed to be internal to the amplification primers. The 3' end of one probe is labelled with a donor fluorophore while the 5' end of an adjacent probe is labelled with an acceptor fluorophore. When the two probes are specifically hybridised in closed proximity (spaced by 1 to 5 nucleotides) the donor fluorophore which has been excited by an external light source emits light that is absorbed by a second acceptor that emit more fluorescence and yields a fluorescence resonance energy transfer (FRET) signal. Molecular beacon probes possess a stem-and-loop structure where the loop is the probe and at the bottom of the stem a fluorescent moiety is at one end while a quenching moiety is at the other end. The molecular beacons undergo a fluorogenic conformational change when they hybridise to their targets hence separating the fluorochrome from its quencher. The FRET principle has been used for real-time detection of PCR amplicons in an air thermal cycler equipped with a built-in fluorometer (Wittwer, C T. et al. 1997, BioTechniques 22:130-138). Apparatus for real-time detection of PCR amplicons are capable of rapid PCR cycling combined with either fluorescent intercalating agents such as SYBR® Green I or FRET detection. Methods based on the detection of fluorescence are particularly promising for utilisation in routine diagnosis as they are very simple, rapid and quantitative.

The probe(s) used may thus comprise a component comprising at least one detectable label. The detectable label may be capable of producing an optical signal. Alternatively, the detectable label may comprise a fluorophore. Examples of fluorophores include but are not limited to fluorescent proteins, for example GFP (green fluorescent protein), YFP (yellow fluorescent protein), RFP (red fluorescent protein); non-protein fluorophores selected from the group consisting of xanthene derivatives (for example, fluorescein, rhodamine, Oregon green, eosin, 6-carboxyfluorescein and Texas red); cyanine derivatives (for example, cyanine, indocarbo-cyanine, oxacarbocyanine, thiacarbocyanine, and merocyanine), squaraine derivatives and ring-substituted squaraines, including Seta, SeTau, and Square dyes, naphthalene derivatives (dansyl and prodan derivatives), coumarin derivatives, oxadiazole derivatives (for example pyridyloxazole, nitrobenzoxadiazole and benzoxadiazole), anthracene derivatives (for example anthraquinones, DRAQ5, DRAQ7 and CyTRAK Orange), pyrene derivatives (for example cascade blue), oxazine derivatives (for example, Nile red, Nile blue, cresyl violet, oxazine 170), acridine derivatives (for example proflavin, acridine orange, acridine yellow), arylmethine derivatives (for example auramine, crystal violet, malachite green), tetrapyrrole derivatives (for example porphin, phthalocyanine, bilirubin) and derivatives thereof. Preferably, the fluorophore is selected from the group consisting of FAM (carboxyfluorescein), TET (carboxy-2',4,7,7'tetrachlorofluorescein succinimidyl ester), HEX (carboxy-2,4,4,5,7,7-hexachlorofluorescein succinimidyl ester), ROX (carboxy-X-rhodamine) and NED. More preferably, the fluorophore is FAM (carboxyfluorescein), or 6-FAM (6-carboxyfluorescein). The at least one detectable label is advantageously capable of producing a changeable signal. The changeable signal may be produced upon the hybridisation of the probe to the target sequence. For example, the signal may be detectable before the probe binds to the target sequence, and upon the hybridisation of the probe to the target sequence, the signal is reduced in strength or becomes completely undetectable. In another example, the detectable signal may be produced only upon the hybridisation of the probe to the target sequence, or the strength of the detectable signal may be increased upon the hybridisation of the probe to the target sequence.

In some instances, it may be advantageous to use a component comprising two detectable labels. The two detectable labels may function independently. Alternatively, the two detectable labels may be an interactive pair of labels, which are preferably capable of generating a changeable signal. For example, the signal may be detectable before the probe binds to the target sequence, and upon the hybridisation of the probe to the target sequence, the signal is reduced in strength or becomes completely undetectable. Alternatively, the detectable signal may be produced only upon the hybridisation of the probe to the target sequence, or the strength of the detectable signal may be increased upon the hybridisation of the probe to the target sequence. In one specific example, the detectable signal is not generated when both detectable labels are linked together by the probe sequence. Once at least one detectable label is cleaved from the probe, the detectable signal is generated.

Preferably, the interactive pair of labels may comprise a fluorophore and a quencher pair. In one specific aspect, the fluorophore may be located at the 5' end of the probe, and the quencher may be located at the 3'end of the probe. Examples of quenchers include but are not limited to TAMRA (tetramethylrhodamine), TaqMan® MGB (minor groove binder) and BHQ™ (Black Hole Quencher™). In one specific example, the fluorophore is FAM (carboxyfluorescein), more particularly 6-FAM (6-carboxyfluorescein), and the quencher is TAMRA (tetramethylrhodamine).

The probe(s) used in the method disclosed herein has a length of at least 5, at least 10, at least 15, or at least 20 nucleotides. Alternatively, the length of the probe(s) used in the present method is less than 40, less than 35, less than 30, or less than 25 nucleotides. The length of the probe(s) may also be comprised between 5 and 40 nucleotides, or between 10 and 35 nucleotides, or between 15 and 30 nucleotides, or between 20 and 25 nucleotides. In yet another aspect, the probe(s) used in the method described herein are 8 nucleotides, or 9 nucleotides, or 10 nucleotides, or 12 nucleotides, or 14 nucleotides, or 16 nucleotides, or 18 nucleotides, or 20 nucleotides, or 22 nucleotides, or 24 nucleotides, or 26 nucleotides, or 28 nucleotides, or 30 nucleotides, or 32 nucleotides, or 34 nucleotides, or 36 nucleotides, or 38 nucleotides, or 40 nucleotides long. Preferably, the probe may have a G or C at the 5' end.

In a particular embodiment, probes nucleic acid sequences may advantageously comprise locked nucleic acids (LNA) (modified nucleic acids), in order to increase the melting temperature (Tm) of probes, which will optimize their specificity to the targeted DNA sequence. Mention may be made to the publication of Matthew P. Johnson et al. (Nucleic Acids Research, 2004, Vol. 32, No. 6 e55DOI: 10.1093/nar/gnh046) for the LNA technology. So, in a particular and preferred embodiment, probes used in the method of detection according to the invention are LNA probes. In a specific example, a method for detecting SARS-CoV-2 in a sample of environmental water may comprise using at least one probe selected in the group consisting of:

```
                                    (SEQ ID NO. 1)
ACCCCGCATTACGTTTGGTGGACC, (SEQ ID NO. 2)
ACAATTTGCCCCCAGCGCTTCAG,
and (SEQ ID NO. 3)
ACACTAGCCATCCTTACTGCGCTTCG.
```

As described above, the amplification step is a multiplex PCR amplification that includes the simultaneous amplification of a plurality of target sequences in a single amplification reaction. Thus, at least 2, at least 3, at least 4, at least 5, at least 6, at least 7, at least 8, at least 9, at least 10, at least 15, at least 20, at least 30, at least 40, or at least 50 sequences are amplified, preferably simultaneously amplified, in step c) of the present method. More specifically, 2, 3, 4, 5, 6, 7, 8, 9, 10, 15, 20, 30, 40, or 50 sequences are amplified, preferably simultaneously amplified, in step c) of the present method. As shown by the inventors, the sensitivity of the method is positively correlated with the number of sequences amplified.

At least some of the target sequences can be situated on the same nucleic acid molecule or on different target nucleic acid molecules included in the single amplification reaction. Therefore, a plurality of target sequences are amplified by a single PCR using a primer pool for amplifying each target sequence. Multiplex PCR assays are well known in the art. See e.g., U.S. Pat. Nos. 5,582,989; 9,921,154, WO 2010/115100; WO 2017/201276.

A set of primers for a multiplex dPCR should be capable of specifically binding to a target sequence and should not interfere with each other in order to amplify the target sequence by a sufficient amount. A multiplex dPCR using such a set of primers saves time, effort and cost for amplifying a target sequence in comparison with a single PCR. Moreover, multiplex dPCR lowers the threshold of detection of nucleic acid in a sample. In particular, even fragments of the pathogen nucleic acid can be detected when several pairs of primers targeting different sequences are used. In other words, multiplex dPCR enables the detection of target sequences even when the starting material is degraded, thereby increasing the sensitivity of the assay.

As used herein, a "primer" refers to a single-stranded oligonucleotide or DNA fragment which hybridises with a nucleic acid strand in such a manner that the 3' terminus of the primer can act as a site of polymerisation and extension using a DNA polymerase enzyme. The primer may be comprised of any combination of nucleotides or analogues thereof, which may be optionally linked to form a linear polymer of any suitable length. A primer may have any suitable length, such as at least about 10, 15, 20, or 30 nucleotides. In some embodiments, primer lengths are in the range of about 10 to about 60 nucleotides, about 12 to about 50 nucleotides, about 15 to about 30 nucleotides, and about 15 to about 40 nucleotides in length. Preferably, the primer length is comprised between 15 and 30 nucleotides. The primer optionally occurs naturally, as in a purified restriction digest, or can be produced synthetically.

In a preferred embodiment, the primers of the invention are produced synthetically. In some embodiments, a primer can be paired with a compatible primer within an amplification or synthesis reaction to form a primer pair consisting or a forward primer and a reverse primer. "Primer pair" thus refers to two primers comprising a forward primer that hybridises to a single strand at one end of the DNA sequence to be amplified, and a reverse primer that hybridises with the other end on the complementary strand of the DNA sequence to be amplified. Optionally, the forward primer primes synthesis of a first nucleic acid strand, and the reverse primer primes synthesis of a second nucleic acid strand, wherein the first and second strands are substantially complementary to each other, or can hybridise to form a double-stranded nucleic acid molecule. In some embodiments, one end of an amplification or synthesis product is defined by the forward primer and the other end of the amplification or synthesis product is defined by the reverse primer. Accordingly, a pair of primers may be a sense primer and an antisense primer that collectively define the opposing ends (and thus the length) of a resulting amplicon.

Typically, a primer is capable of hybridising to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein.

As used herein, "target-specific primer" and its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is substantially non-complementary to other target sequences present in the sample; optionally, the target-specific primer is substantially non-complementary to other nucleic acid molecules present in the sample. In some embodiments, the target-specific primer can include minimal cross hybridisation to other target-specific primers in the amplification reaction. In some embodiments, target-specific primers include minimal cross-hybridisation to non-specific sequences in the amplification reaction mixture. In some embodiments, a forward target-specific primer and a reverse target-specific primer define a target-specific primer pair that can be used to amplify the target sequence via template-dependent primer extension. Preferably, the target-specific primers include minimal self-complementarity. In some embodiments, the primer hybridises to the target sequence within 60 to 200 nucleotides on either side of the sequence bound by the probe.

Primers for amplification within a partition can have a concentration of about 0.1, 0.2, 0.3, 0.4, 0.5, 0.6, 0.7, 0.8, 0.9, or 1.0 μM. The concentration of each primer can be about 0.5 μM. Primers can be designed according to known parameters for avoiding secondary structures and self-hybridisation. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridise to the genetic targets described herein. About 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers can be used.

Primers can be prepared by a variety of methods including but not limited to cloning of appropriate sequences and direct chemical synthesis using methods well known in the art (Narang et al, Methods Enzymol. 68:90 (1979); Brown et al, Methods Enzymol. 68:109 (1979)). Primers can also be obtained from commercial sources such as Integrated DNA Technologies, Operon Technologies, Amersham Pharmacia Biotech, Sigma, or Life Technologies.

The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. The melting temperature of a primer can be about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C. Preferably, the melting temperature of a primer is comprised between 5° and 65° C. advantageously, the melting temperature of a primer is lower than the melting temperature of the probe by 3 to 10° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. For example, the primer may contain a G or C as the 3' extremity. In another instance, the primer may contain between 50 and 60% G/C. In yet another instance, the primer does not contain sequences of repeated G/C triplets. An equation for determining the melting temperature of primers smaller than 25 base pairs is the Wallace Rule (Td=2 (A+T)+4 (G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer (free web based program at premierbiosoft-.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the TM can be recalculated based on both the sequences of the 5' half and the 3' half of each primer.

For example, primers that can be used for detecting SARS-CoV-2 in a sample of an environmental water matrix may include at least one, at least two, at least three, at least four, at least five, or at least six primers selected in the group consisting of:

```
                                      (SEQ ID NO. 4)
        GACCCCAAAATCAGCGAAAT, (SEQ ID NO. 5)
        TCTGGTTACTGCCAGTTGAATCTG, (SEQ ID NO. 6)
        TTACAAACATTGGCCGCAAA, (SEQ ID NO. 7)
        GCGCGACATTCCGAAGAA, (SEQ ID NO. 8)
        ACAGGTACGTTAATAGTTAATAGCGT,
        and (SEQ ID NO. 9)
        ATATTGCAGCAGTACGCACACA.
```

More preferably, detecting SARS-CoV-2 in a sample of an environmental water matrix according to the method of the invention comprises using all six of the following primers:

```
                                      (SEQ ID NO. 4)
        GACCCCAAAATCAGCGAAAT, (SEQ ID NO. 5)
        TCTGGTTACTGCCAGTTGAATCTG, (SEQ ID NO. 6)
        TTACAAACATTGGCCGCAAA, (SEQ ID NO. 7)
        GCGCGACATTCCGAAGAA, (SEQ ID NO. 8)
        ACAGGTACGTTAATAGTTAATAGCGT,
        and (SEQ ID NO. 9)
        ATATTGCAGCAGTACGCACACA.
```

In another embodiment, the invention concerns a method of detecting *Escherichia coli* in a sample of an environmental water matrix.

For example, primers that can be used for detecting *Escherichia coli* in a sample of an environmental water matrix may include at least one of the following primers:

```
                                      (SEQ ID NO: 17)
        CCAGTTTGCGTTCAATACCG (SEQ ID NO: 18)
        GTCGCTAGAAAACGTCCGTA
```

Preferably, the multiplex dPCR reaction comprises using a primer set comprising:

```
                                      (SEQ ID NO: 17)
        CCAGTTTGCGTTCAATACCG (SEQ ID NO: 18)
        GTCGCTAGAAAACGTCCGTA
```

In a particular embodiment, the multiplex dPCR reaction comprises further using at least one probe of sequence

```
                                      (SEQ ID NO: 27)
        CCTGCCGCGTTGGCAATGTCGAGT.
```

Specifically, the present method may comprise a further step of quantifying the amount of a SARs-COV-2 (or any other pathogen) nucleic acid comprising the sequence amplified as described above in the sample of the environmental liquid matrix based on the amplification of step c).

In addition to the components listed above, a partition can comprise a polymerase. The polymerase can be a DNA polymerase. Numerous DNA polymerase are known in the art (e.g., T4 DNA polymerase, DNA polymerase I, Klenow Fragment, Phi29 DNA polymerase, T7 DNA polymerase, etc.). The DNA polymerase can comprise 3' to 5' exonuclease activity. The DNA polymerase can comprise 5' to 3' exonuclease activity. The DNA polymerase can comprise both 3' to 5' exonuclease activity and 5' to 3' exonuclease activity. The DNA polymerase can comprise neither 3' to 5' exonuclease activity nor 5' to 3' exonuclease activity. The DNA polymerase can comprise strand displacement activity. In some cases, the DNA polymerase does not comprise strand displacement activity. Examples of polymerases which can be used in the present method include a Bst DNA Polymerase, a Full Length, a Bst DNA Polymerase, a Large Fragment, a Bsu DNA Polymerase, a Crimson Taq DNA Polymerase, a Large Fragment, Deep VentR™, a DNA Polymerase, a Deep VentR™ (exo-), a DNA Polymerase, a *E. coli* DNA Polymerase I, a Klenow Fragment (3'→5' exo-), a DNA Polymerase I, a Large (Klenow) Fragment, a LongAmp® Taq DNA Polymerase or Hot Start, a M-MuLV Reverse Transcriptase, a OneTaq® DNA Polymerase or Hot Start, a phi29 DNA Polymerase, a Phusion® Hot Start Flex DNA Polymerase, a Phusion® High-Fidelity DNA Polymerase, a Q5®+Q5® Hot Start DNA Polymerase, a *Sulfolobus* DNA Polymerase IV, a T4 DNA Polymerase, a T7 DNA Polymerase, a Taq DNA Polymerase, a Therminator™ DNA Polymerase, a VentR® DNA Polymerase, a VentR® (exo-) DNA Polymerase, and any combination thereof.

Preferably, the DNA polymerase is a thermostable DNA polymerase, such as e.g., Pfu DNA polymerase, Vent DNA polymerase, Pfx DNA polymerase, Taq DNA polymerase, DEEP VENT™ DNA polymerase, LONGAMP® Tag, PHUSION® High Fidelity DNA polymerase, LONGAMP® Hot Start Taq, Crimson LONGAMP® Taq, Crimson Taq DNA polymerase, ONETAQ® DNA polymerase, QUICK-LOAD® DNA polymerase, VENTR® DNA polymerase, Hemo KLENTAQ®, etc.

A partition can comprise a reverse transcriptase. In particular, when the target polynucleotide to be detected is an RNA, a reverse transcriptase may advantageously be added to the partition in order to obtain a cDNA from the mRNA contained in the biological sample. The cDNA obtained will then be used as a target for amplification for the primers used in the method described herein.

One or more reactions may be performed in the partitions. Each reaction performed may occur selectively (and/or substantially) in only a subset of the partitions, such as less than about one-half, one-fourth, or one-tenth of the partitions, among others. The reaction may involve a target, which may, for example, be a template and/or a reactant (e.g., a substrate), and/or a binding partner, in the reaction. The reaction may occur selectively (or selectively may not occur) in partitions containing at least one copy of the target.

The reaction may or may not be an enzyme-catalysed reaction. In some examples, the reaction may be an amplification reaction, such as a polymerase chain reaction and/or ligase chain reaction. Accordingly, a plurality of amplification reactions for a plurality of targets may be performed simultaneously in the partitions.

Performing a reaction may include subjecting the partitions to one or more conditions that promote occurrence of the reaction. Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

The methods of the disclosure can comprise an amplification step using a polymerase chain reaction (PCR). In some applications, there is enough starting material in the sample such that no amplification step is necessarily required.

In some applications, the amplification step of the method performs a forward transcription amplification reaction. In some applications, the amplification step of the method, performs a reverse transcription amplification reaction. In some applications the polymerase acts on a single-stranded nucleic acid molecule. In some applications the polymerase acts on double-stranded nucleic acid molecule.

In most of the methods that include an amplification step, the amplification step generally serves to amplify the double-stranded DNA resulting from the primer extension reaction. The amplification may be conducted using a polymerase chain reaction (PCR) using forward and reverse primers. The PCR reaction may be conducted with a DNA polymerase. In some cases, the DNA polymerase is identical to the DNA polymerase used during the extension Bst primer step (e.g., 2.0 DNA polymerase). In some cases, DNA polymerase is different from the DNA polymerase used in the primer extension step. Any DNA polymerase known in the art may be used for amplification.

Preferably, the PCR amplification for each multiplex can be performed using the same thermal cycling profile thereby allowing the amplification of all the nucleic acid targets at the same time (simultaneously) in a single apparatus (e.g., thermocycler).

As used herein, the expression "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and themocycling conditions. In some embodiments, the conditions suitable for amplifying one or more nucleic acid sequences includes polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridised to the nucleic acid. The amplification conditions can require hybridisation or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc.) and can also include various modifiers of ionic strength.

However, as used herein, the term "amplification condition" refers to temperature and/or incubation time suitable to obtain a detectable amount of the target. Therefore, the term "similar amplification conditions" means that the assay may be performed, if desired, under similar temperature for each target. The term "similar amplification conditions" also means that the assay may be performed, if desired, under similar incubation time for each target. The term "similar amplification conditions" may in some instances also refer to the number of amplification cycles. However, it is well known in the art that number of cycles is not always critical. For example, some samples may be removed before others or left for additional amplification cycles. The term "similar amplification conditions" may also refer to the nature of buffer and amplification reagents used (enzyme, nucleotides, salts, etc.). The term "similar amplification conditions" also means that the conditions (e.g., time, buffer, number of cycles, temperature, etc.) may be varied slightly or may be the same.

Exemplary embodiments of amplification conditions are provided in Example section.

In a particular aspect of the method provided herein, the multiplex dPCR comprises amplifying not only sequences of the pathogen nucleic acid of interest, but also at least one sequence of an unrelated nucleic acid. Accordingly, a control sequence that is known or expected to be present in sample, and/or that has a known or expected representation with respect to a bulk nucleic acid population present in the sample (e.g., total DNA, total genomic DNA, genomic DNA from a particular species of organism, total RNA, total mRNA, etc.), may be amplified in the multiplex PCR assay. In contrast, target reagents may amplify a test target that has an unknown presence in the sample and/or an unknown presence in with respect to the bulk nucleic acid population. In any event, amplification of the control sequence may be used to determine the quality of test data measured from a sample, such as to verify the quantitative accuracy of the test data and/or to determine the reliability of the test data. In some embodiments, a control sequence is selected that is rare in the sample, such as a target representing a particular gene mutation. By selecting a rare control sequence, amplification of the control sequence can indicate the limit of detection of a test target and/or whether amplification of a low-abundance test target can occur. In some embodiments, the control sequence may be replaced by a second test target with an unknown presence in the sample (before testing).

Control sequence reagents may be similar in general structure to the test target reagents, but different with respect to the nucleic acid sequences of the primers and probes, to provide test target and control target specificity, respectively. Also, the test and control probes may include distinct dyes and/or distinct energy transfer partners (e.g., distinct quenchers suitable for the respective dyes). In other embodiments, at least one of the probes may be replaced by a reporter including an intercalating dye, such as SYBR Green.

The control sequence may be a positive control of sample preparation, nucleic acid extraction, and amplification. Such a positive control may be useful when no amplification is observed in partitions with control target reagents. In contrast, if the control data identifies positive partition signals, it demonstrates that amplification in the partitions is not inhibited substantially and suggests that the lack of positive signals from the test data is due to an absence or undetectable level of the test target in the sample. Accordingly, the control data supports and helps to validate the negative result in the test data. In contrast, if no amplification of the control sequence, it indicates that amplification of the test target also is defective, and that the negative test result is not valid.

Furthermore, an amount of control sequence determined to be present in the sample may provide a standard against which an amount of test target determined to be present in the sample can be compared and/or normalised.

The skilled person will immediately realise that the control nucleic acid may depend upon the pathogen of interest. For example, murine hepatitis virus (MHV) may serve as a surrogate in methods of detecting SARS-CoV-2 in untreated wastewater (Ahmed et al., 2020, *Sci Total Environ.* 739: 139960). Accordingly, MHV can be added to the sample of environmental water before step a). Preferably, a defined amount of MHV is added to the sample of environmental water before step a).

Alternatively, the skilled person can use the pepper mild mottle virus (PMMoV) as a control in the method described herein. This virus, and is a plant virus belonging to the genus *Tobamovirus* in the family Virgoviridae and has the advantage of being the most abundant RNA virus in human faeces. It is excreted from a large proportion of healthy human populations, but rarely found in animal faeces. Thus a particular aspect of the method disclosed herein comprises the amplification of at least one PMMOV sequence in addition to at least one SARS-CoV-2 (or other pathogen) sequence in the multiplex dPCR assay. Preferably, this multiplex dPCR assay comprises using at least one probe of sequence: CCTACCGAAGCAAATG (SEQ ID NO. 10). In another instance, the multiplex dPCR reaction comprises using a primer set comprising: GAGTGGTTTGACCT-TAACGTTTGA (SEQ ID NO. 11) and TTGTCGGTTGCAATGCAAGT (SEQ ID NO. 12). In yet another instance, the multiplex dPCR reaction comprises using at least one probe of sequence:

CCTACCGAAGCAAATG (SEQ ID NO. 10), and using a primer set comprising: GAGTGGTTTGACCT-TAACGTTTGA (SEQ ID NO. 11) and TTGTCGGTTGCAATGCAAGT (SEQ ID NO. 12). The present method may comprise a further step of quantifying the amount of a nucleic acid comprising the sequence amplified with the primers: GAGTGGTTTGACCT-TAACGTTTGA (SEQ ID NO. 11) and TTGTCGGTTGCAATGCAAGT (SEQ ID NO. 12), in the sample of the environmental liquid matrix, based on the amplification of step c).

Because the presence of PMMOV is fairly constant in human faeces, this virus is particularly useful as a control for the present method, notably as a way to normalise data obtained by the present method. Specifically, the data generated by the amplification of the SARS-CoV-2 (or another pathogen) sequences can be normalised to the data of the amplification of PMMOV. Preferably, the number of copies of SARS-CoV-2 (or another pathogen to be detected) in the environmental water sample measured by the method can be normalised to the number of copies of the PMMOV measured through the same assay. The resulting normalised data can then be compared with normalised data obtained for a different water matrix or for the same water matrix at a different time.

Accordingly, the present method comprises a further step of normalising the amount of SARS-CoV-2 (or another pathogen to be detected) nucleic acid to the amount of PMMOV nucleic acid. More specifically, the amount of SARS-CoV-2 nucleic acid which is quantified is the amount of a SARs-CoV-2 nucleic acid comprising the sequence amplified with at least one, at least two, at least three, at least four, at least five, or at least six primers selected in the group consisting of:

```
                                    (SEQ ID NO. 4)
        GACCCCAAAATCAGCGAAAT, (SEQ ID NO. 5)
        TCTGGTTACTGCCAGTTGAATCTG, (SEQ ID NO. 6)
        TTACAAACATTGGCCGCAAA, (SEQ ID NO. 7)
        GCGCGACATTCCGAAGAA, (SEQ ID NO. 8)
        ACAGGTACGTTAATAGTTAATAGCGT,
        and (SEQ ID NO. 9)
        ATATTGCAGCAGTACGCACACA.
```

Likewise, the amount of PMMOV nucleic acid which is quantified is the amount of a nucleic acid comprising the sequence amplified with the primers: GAGTGGTTTGACCTTAACGTTTGA (SEQ ID NO. 11) and TTGTCGGTTGCAATGCAAGT (SEQ ID NO. 12).

SARS-CoV-2 has already been detected in wastewater. Its detection precedes the first reported case and its abundance tracked the rise and fall of cases seen in SARS-CoV-2 clinical test results and local COVID-19 hospital admissions (Medema et al., 2020, *Environ Sci Technol Lett.* 20:511-516; Randazzo et al., 2020, *Water Res.*181:115942; Peccia et al., 2020, *Nat. Biotechnol.* 38:1164-1167).

In another aspect, the present disclosure relates to a method of detecting a pathogen infection in a human population, comprising detecting of said pathogen in wastewater according to the method described above.

In a preferred embodiment, the present disclosure relates to a method of detecting a SARS-CoV-2 infection in a human population, comprising detecting SARS-CoV-2 in wastewater according to the method described above.

In another embodiment, the present disclosure relates to a method of detecting a *Escherichia coli* infection in a human population, comprising detecting *Escherichia coli* in wastewater according to the method described above.

Hereinbelow, the present invention is explained in detail in view of the examples. However, the following examples are given only for exemplification of the present invention, and it is evident that the present invention is not limited to the following examples.

EXAMPLES

Example 1: Detection and Quantification of SARS-CoV-2 in Wastewater

The present examples illustrate the detection and quantification of SARS-CoV-2 in wastewater. The results are expressed in number of copies per liter of sample.

Material and Methods

Sampling

Samples are taken over a period of 24 hours at 4 sampling sites, with contrasted viral concentrations (from high in samples from STEP Maera & positive control to low in STEP of Bassin de Thau) and contrasted load of PCR inhibitors (from high in STEP to middle in Hospital building):

Station d'épuration des eaux usées (STEP) of Maera (France), >400 000 PE (person equivalent);

Station d'épuration des eaux usées (STEP) of Bassin de Thau (France), <100 000 PE (person equivalent);

Hospital building for COVID 19 patients (Montpellier, France)—positive control; and Hospital building not hosting any COVID-19 patient (Montpellier, France)—negative control.

The samples were kept at 4° C. until further treatment unless otherwise mentioned. The sample volumes taken are comprised between 100 mL and 1 L.

Sample Treatment

The sample is thoroughly mixed. 30 mL are taken from the homogenised sample and vortexed 3 times for 15 seconds each. The sample is cooled on ice for 15 seconds between each vortex burst.

An Amicon® Ultra-15 Centrifugal Filter Unit (cutoff: 10 kDa) is hydrated with 10 mL of RNase-free water preheated at 70° C. and spun for 20 min at 3234 g, at 4° C.

15 mL are taken from the vortexed sample and applied to the Amicon® Ultra-15 Centrifugal Filter Unit. The tube is then centrifuged for 45 minutes at 3234 g, at 4° C. The resulting volume is inferior to 500 μL. If not, the tube is spun again for 10 minutes at 3234 g, at 4° C. This step is repeated until a volume comprised between 150 to 500 μL is obtained.

RNA Extraction

150 μL of treated sample is used to extract RNA with the NucleoSpin RNA Virus kit (Macherey-Nagel, Germany) according to the manufacturer's instructions in order to obtain 60 μL eluted RNA template.

Multiplex dPCR

RNA is analysed by multiplex dPCR. Each individual reaction contains 1 μL of the total volume of 60 μL eluted RNA template (meaning that 0.75 to 2.5% of each sewage sample is analysed with each RT-dPCR), 5 μL of RT-ddPCR SUPERMIX (Biorad, Marnes-la-Coquette, France), 2 μL of primers 900 μM (see below), 1 μL of DTT 300 mM (Biorad, Marnes-la-Coquette, France), 2 μL of Reverse Transcriptase (Biorad, Marnes-la-Coquette, France), and 1 μL of each probe and the reaction volume was adjusted to a final volume of 20 μL with RNAse free distilled water.

The primers used in the reaction have been previously published. They comprise the N1-N2 set from CDC that each target a different region of the nucleocapsid (N) gene and the set targeting the envelope protein (E) gene from Corman et al. (Corman et al., 2020, *Euro Surveill*. 25 (3): 2000045), to include targets against two separate SARS-CoV-2 genes. The specificity of these primer/probe sets against other (respiratory) viruses, including human coronaviruses, was previously confirmed (Corman et al., 2020, *Euro Surveill*. 25 (3): 2000045; www.fda.gov; Medema et al., 2020, *Environ Sci Technol Lett*. 20:511-516). Specifically, the following primers are used:

```
                                        (SEQ ID NO. 4)
          GACCCCAAAATCAGCGAAAT, (SEQ ID NO. 5)
          TCTGGTTACTGCCAGTTGAATCTG, (SEQ ID NO. 6)
          TTACAAACATTGGCCGCAAA, (SEQ ID NO. 7)
          GCGCGACATTCCGAAGAA, (SEQ ID NO. 8)
          ACAGGTACGTTAATAGTTAATAGCGT,
          and (SEQ ID NO. 9)
          ATATTGCAGCAGTACGCACACA.
```

The following probes are used at a concentration of 250 nM:

```
                                        (SEQ ID NO. 1)
          ACCCCGCATTACGTTTGGTGGACC, (SEQ ID NO. 2)
          ACAATTTGCCCCCAGCGCTTCAG,
          and (SEQ ID NO. 3)
          ACACTAGCCATCCTTACTGCGCTTCG.
```

The fluorochromes are FAM, HEX, and HEX 50% FAM 50%, respectively.

Emulsion droplets are generated with the QX200 Droplet Digital PCR System (Biorad, Marnes-la-Coquette, France) according to the manufacturer's instructions.

Thermal cycling reactions were carried out at 50° C. for 60 minutes, then 95° C. for 10 minutes, followed by 40 cycles of 95° C. for 30 seconds and 58° C. for 1 minute, and concluded at 98° C. for 10 minutes, on the T100 PCR thermal cycler (Biorad).

Data are analysed with the QuantaSoft Software (Biorad, Marnes-la-Coquette, France). The results are expressed in number of copies per liter of sample.

Results

In a first series of experiments, it was investigated whether the samples could be kept above 4° C. before between sampling and treatment. For each sampling site, three identical samples were kept at:

4° C. for 24 hours;

21° C. for 24 hours, or.

21° C. for 48 hours.

No difference was observed between the three set of conditions in all samples (FIG. 1), indicating that the storage temperature does not affect significantly the sensitivity of the method.

In a second series of experiments, the effect of the clarification step was tested. The samples were divided in three:

the first one was subjected to a centrifugation at >4000 G before concentration on the Amicon® Ultra-15 Centrifugal Filter Unit (cutoff: 10 kDa);

the second was subjected to a centrifugation at <4000 G before concentration on the Amicon® Ultra-15 Centrifugal Filter Unit (cutoff: 10 kDa); and the third was not clarified before concentration on the Amicon® Ultra-15 Centrifugal Filter Unit (cutoff: 10 kDa).

Figure 2:
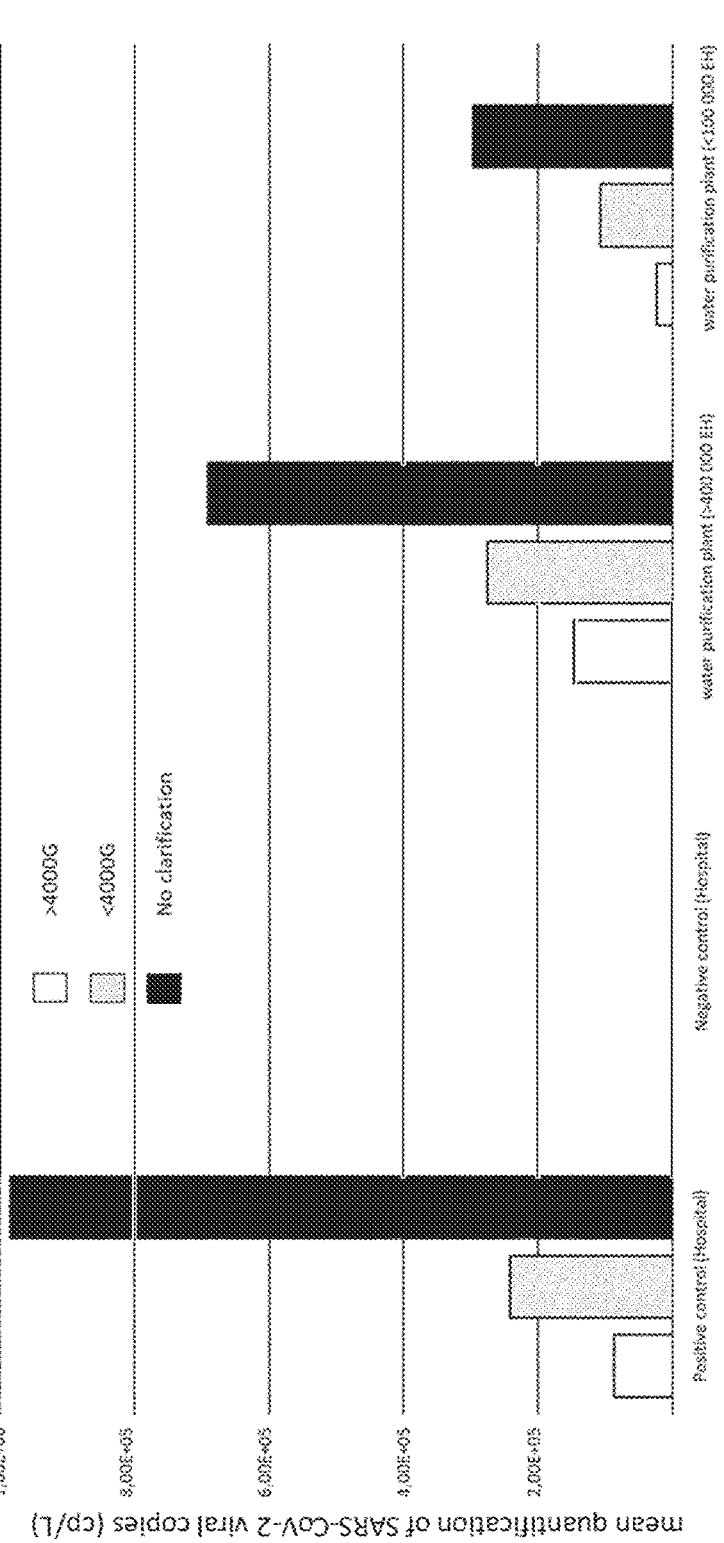
FIG. 2: Evaluation of the clarification step on the yield of the method.

The results (FIG. 2) show clearly that clarification has a negative impact on the yield of the reaction, whatever the centrifugation characteristics. By comparison, higher number of viral copies were consistently detected in the untreated sample. Thus, the clarification step decreases the sensitivity of the assay.

In a third series of experiments, the influence of the concentration step on the assay yield was investigated. Filters with two different cutoffs were compared: 10 kDa and 100 kDa.

Figure 3:
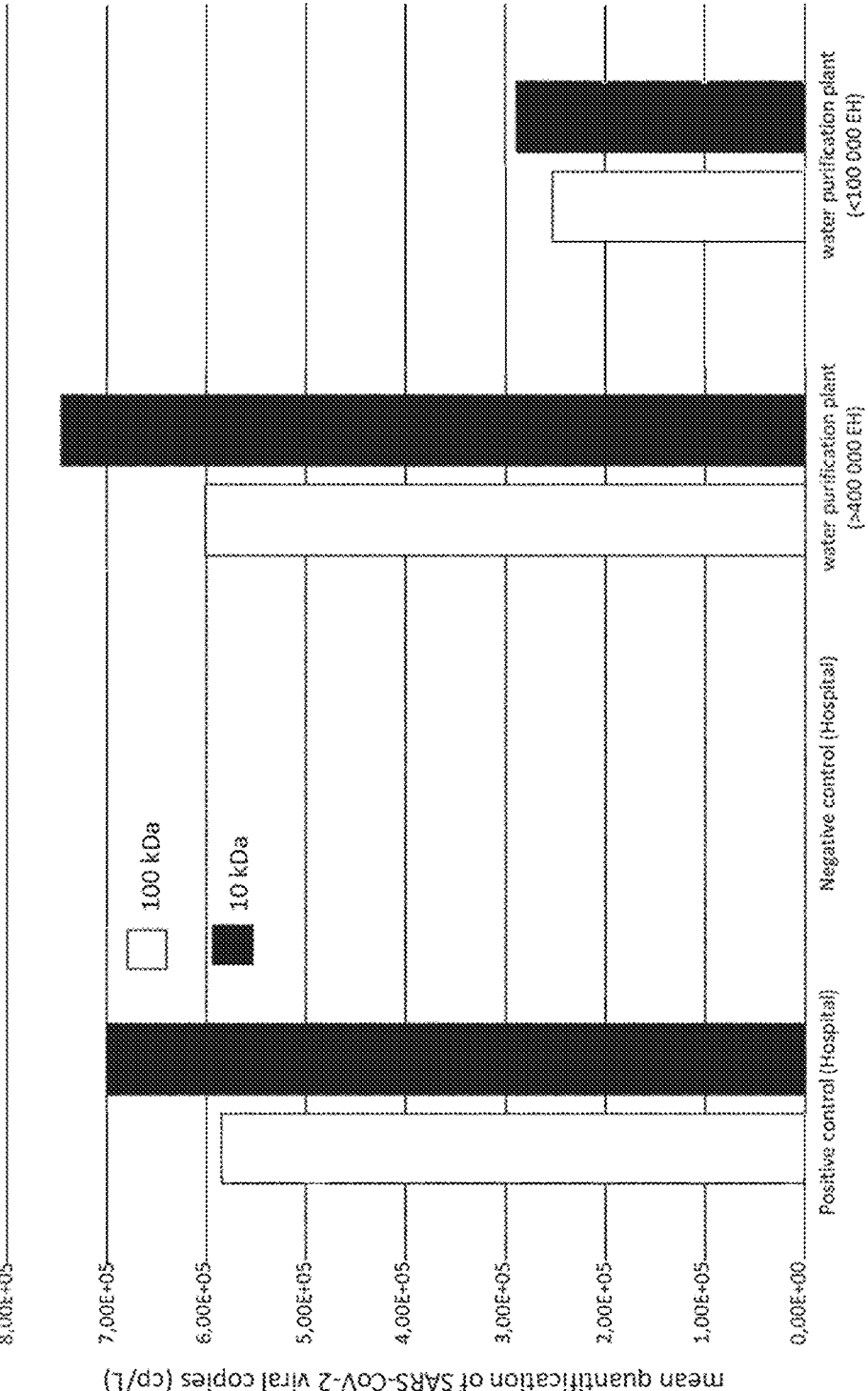
FIG. 3: Evaluation of the concentration step on the yield of the method.

As shown in FIG. 3, higher number of viral copies were consistently detected in the sample concentrated on a filter with a 10 kDa cutoff.

In a fourth series of experiments, the impact of the number of sequences tested in the multiplex dPCR was tested. Serial dilutions of a sample obtained from a positive control were tested either in a duplex or a triplex dPCR amplification.

Figure 4:
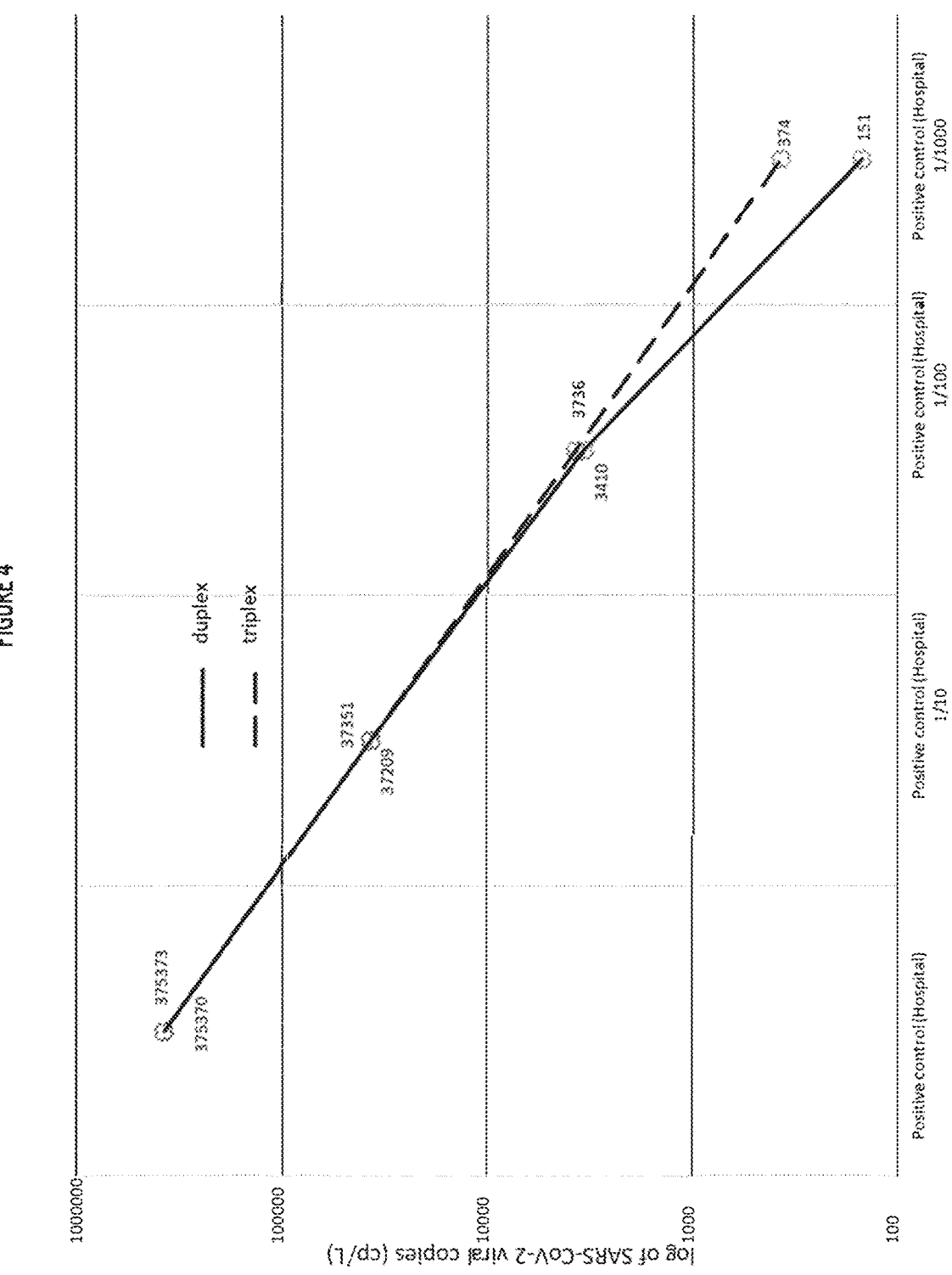
FIG. 4: Evaluation of the number of sequences amplified in the multiplex dPCR reaction on the sensitivity of the method.

The results show unambiguously that the sensitivity of the assay is improved by amplifying three sequences instead of two, especially for low concentrations of virus linearity is maintained even at the highest dilutions with viral concentrations inferior to $3.4 \times 10^3$ cp/L, whereas it is lost in the duplex reaction (FIG. 4).

Example 2: Detection and Quantification of Other Virus, Bacteria and Fungus in Wastewater This example, based on the same method as disclosed in the example 1 but with other primers and probes specific to the pathogen to be detected, illustrates the detection and quantification of nucleic acid of other virus (RNA virus), bacteria and fungus (DNA) in wastewater samples:

Virus: Hepatite A, Norovirus GI, Norovirus GII
Bacteria: *Enterococcus durans* and *Escherichia coli*
Fungus: *Candida albicans*
Material and Methods
Sampling Samples are taken over a period of 24 hours at different sampling sites, with contrasted bacterial and viral concentrations and contrasted load of PCR inhibitors (from high in STEP to middle in Hospital building):

Station d'épuration des eaux usées (STEP) of Maera (France), >400 000 PE (person equivalent), (Maera-E);

Station d'épuration des eaux usées (STEP) of AGDE (France) (AGD), >52 000 PE (person equivalent) (AGD);

Station d'épuration des eaux usées (STEP) of BEZIERS (France) (BEZ), >130 000 PE (person equivalent) (BEZ);

Station d'épuration des eaux usées (STEP) of Grau du Roi (France), >100 000 PE (person equivalent) (ZR2 & ZR30);

Station d'épuration des eaux usées (STEP) of La Grande Motte (France) (LGM), >65 000 PE (person equivalent) (LGM);

Hospital building for COVID 19 patients (Montpellier, France) (CHU-S);

Hospital building not hosting any COVID-19 patient (Montpellier, France) (CHU-N);

Positive control Norovirus (inactivated virus): NATNOV-6MC, zeptometrix;

Positive control *Escherichia coli* (referenced bacterial strain ATCC 11775);

Positive control *Escherichia coli* (referenced bacterial strain ATCC 25922);

Positive control *Enterococcus durans* BSL2 (referenced bacterial strain CIP 55.125T).

The samples were kept at 4° C. until further treatment unless otherwise mentioned. The sample volumes taken are comprised between 100 mL and 1 L.
Sample Treatment The sample is thoroughly mixed. 30 mL are taken from the homogenised sample and vortexed 3 times for 10 seconds each. The sample is cooled on ice for 15 seconds between each vortex burst.

An Amicon® Ultra-15 Centrifugal Filter Unit (cutoff: 10 kDa) is hydrated with 2.5 mL of MQ water and spun for 10 min at 3234 g, at 4° C.

15 mL are taken from the vortexed sample and applied to the Amicon® Ultra-15 Centrifugal Filter Unit. The tube is then centrifuged for 35 minutes at 3234 g, at 4° C. The resulting volume is inferior to 500 µL. If not, the tube is spun again for 10 minutes at 3234 g, at 4° C. This step is repeated until a volume comprised between 150 to 500 µL is obtained.
RNA Extraction
Nucelospin RNA Virus Kit 150 µL of treated sample is used to extract nucleic acid with the NucleoSpin RNA Virus kit (Macherey-Nagel, Germany) according to the manufacturer's instructions in order to obtain 60 µL eluted nucleic acid template.

NuceloMag DNA/RNA Water 200 µL of treated sample is used to extract nucleic acid with the NucleoMag DNA/RNA Water (Macherey-Nagel, Germany) according to the manufacturer's instructions in order to obtain 100 µL eluted nucleic acid template.

Automate: IDEAL™ 32 (ID.vet, French)
IndiMag Pathogen Kit

200 µL of treated sample is used to extract DNA/RNA with the IndiMag Pathogen Kit (Indical, Germany) according to the manufacturer's instructions in order to obtain 100 µL eluted nucleic acid template.

Automate: IndiMag® 48 (Indical, French)

RNA is analysed by multiplex dPCR (Multiplex dPCR for Nanoplate 26K 24-well (Qiagen, Germany). Each individual reaction contains 4 µL of the total volume of 60 µL eluted RNA template (meaning that 0.75 to 2.5% of each sewage sample is analysed with each RT-dPCR), 10 µL of One-Step Viral RT-PCR Master Mix (QIAGEN), 0.4 µL Multiplex Reverse Transcription Mix, and 1 µL of mix probe (5 µM)/primer (18 µM) and the reaction volume was adjusted to a final volume of 40 µL with RNAse free distilled water.

DNA is analysed by multiplex dPCR (Multiplex dPCR for Nanoplate 26K 24-well (Qiagen, Germany). Each individual reaction contains 4 µL of the total volume of 60 µL eluted DNA template (meaning that 0.75 to 2.5% of each sewage sample is analysed with each RT-dPCR), 10 µL of QIAcuity Probe PCR kit (QIAGEN), and 1 μL of mix probe (5 μM)/primer (18 μM) and the reaction volume was adjusted to a final volume of 40 μL with RNAse free distilled water.

Specifically, the following primers are used at a concentration of 450 nM:

TABLE 1

| Target | Forward (5'->3') | Reverse (5'->3') |
|---|---|---|
| *Enterococcus durans* | TTATGTC CCAGTAT TGAAAAA TCAA (SEQ ID NO: 13) | GTGAATC ATATTGG TATGCAG TC (SEQ ID NO: 14) |
| Hepatitis A virus | TCACCGC CGTTTGC CTAG (SEQ ID NO: 15) | GGAGAGC CCTGGAA GAAAG (SEQ ID NO: 16) |
| *Escherichia coli* | CCAGTTT GCGTTCA ATACCG (SEQ ID NO: 17) | GTCGCTA GAAAACG TCCGTA (SEQ ID NO: 18) |
| Norovirus GI | GCTGGAT GCGCTTC CAT (SEQ ID NO: 19) | CCTTAGA CGCCATC ATCATTT AC (SEQ ID NO: 20) |
| Norovirus GII | ATGTTCA GATGGAT GAGATTC TCAGA (SEQ ID NO: 21) | TCGACGC CATCTTC ATTCACA (SEQ ID NO: 22) |
| *Candida albicans* | TTGGTAT TTTGCAT GTTGCTC (SEQ ID NO: 23) | GTCAGAG GCTATAA CACACAG 20 (SEQ ID NO: 24) |

The following probes are used at a concentration of 150 nM:

TABLE 2

| Target | Probe (5'-> 3') | Fluorochrome | Quencher |
|---|---|---|---|
| *Enterococcus durans* | CGTAGGG ATCTCCA AAGCGGA AAATCGG (SEQ ID NO: 25) | ROX | BHQ-2 |
| Hepatitis A virus | CCTGAAC CTGCAGG AATTAA (SEQ ID NO: 26) | Cy5 | BHQ-3 |
| *Escherichia coli* | CCTGCCG CGTTGGC AATGTCG AGT (SEQ ID NO: 27) | HEX | BHQ-1 |

TABLE 2-continued

| Target | Probe (5'-> 3') | Fluorochrome | Quencher |
|---|---|---|---|
| Norovirus GI | CGGATTG TGGACAG GAGATCG CGATCTT C (SEQ ID NO: 28) | ROX | 3IAbRQSp |
| Norovirus GII | GAGCACG TGGGAGG GCGATCG C (SEQ ID NO: 29) | FAM | 3IABKFQ |
| *Candida albicans* | TTTACCG GGCCAGC ATCGGTT T (SEQ ID NO: 30) | FAM | BHQ-1 |

The probes listed in the Table 2 for Hepatitis A, *Enterococcus durans* and *Candida albicans* are known from the art:

Costafreda et al., 2006, norme 15216, Appl Environ Microbiol, 2006 June; 72 (6): 3846-55, doi: 10.1128/AEM.02660-05, for Hepatitis A;

E. Knijff et al., J Microbiol Methods, 2001 October; 47 (1): 35-40, doi: 10.1016/s0167-7012 (01) 00297-4, for *Enterococcus durans*; and Brinkman et al., 2003. App Env Microbiol, vol69 (3): 1775-1782 doi: 10.1128/AEM.69.3.1775-1782.2003 for *Candida albicans*.

As these probes were previously validated by scientific community, there is no need of an additional positive control for these pathogens, in the method of detection according to the invention.

RT-PCR Cycle

Thermal cycling reactions were carried out at 50° C. for 40 minutes, then 95° C. for 2 minutes, followed by 40 cycles of 95° C. for 5 seconds and 58° C. for 1 minute Qiagen (Qiacuity).

PCR Cycle

Thermal cycling reactions were carried out at 95° C. for 2 minutes, followed by 40 cycles of 95° C. for 15 seconds and 58° C. for 1 minute Qiagen (Qiacuity).

Data were analysed with the QIAcuity software suite v3 (Qiagen, Germany).

Results

The results are presented in the following tables.

TABLE 3

| | Number of copies detected (per liter of sample) Hepatite A |
|---|---|
| Maera-E 20/07/2020 | 0.00E+00 |
| Maera-E 28/09/2020 | 1.66E+04 |
| Maera-E 26/01/2021 | 8.11E+03 |
| Maera-E 19/04/2021 | 1.99E+04 |

These results demonstrate that we can monitor the detection and quantification of the hepatite A in wastewater of a local site with the present invention.

TABLE 4

| | Number of copies detected (per liter of sample) Norovirus GII |
| --- | --- |
| T POS Norovirus (positive control) | 6.20E+05 |
| AGD_29-09-2021 | 4.94E+04 |
| AGD_04-10-2021 | 6.31E+04 |
| BEZ_01-10-2021 | 8.78E+05 |

These results demonstrate that we can monitor the detection and quantification of the Norovirus GII in wastewater of both local sites geographically closed, with the present invention.

TABLE 5

| | Number of copies detected (per liter of sample) Norovirus GI |
| --- | --- |
| T POS Norovirus (positive control) | 1.51E+06 |
| AGD_29-09-2021 | 3.10E+03 |
| AGD_04-10-2021 | 1.40E+04 |
| BEZ_01-10-2021 | 4.69E+05 |
| LGM_05-10-2021 | 0.00E+00 |

These results demonstrate that we can quantify the Norovirus GI in wastewater of different sites (Agde, Beziers, La Grande Motte) and monitor, for a local site, the evolution of number of viral copies (diminution of number of copies), with the present invention, for adapted measures of prevention and/or treatment.

TABLE 6

| | Number of copies detected (per liter of sample) Escherichia coli |
| --- | --- |
| T POS Escherichia coli ATCC 11775 (positive control) | 6.34E+08 |
| T POS Escherichia coli ATCC 25922 (positive control) | 5.06E+08 |
| BEZ_04-10-2021 | 7.04E+04 |
| LGM_05-10-2021 | 1.22E+07 |
| CHU-S_06-10-2021 | 1.65E+06 |

These results demonstrate that we can quantify *Escherichia coli* in wastewater of different sites (Beziers, La Grande Motte and CHU Montpellier) and demonstrate differences between the sites of sampling, with the present invention, for adapted measures of prevention and/or treatment.

TABLE 7

| | Number of copies detected (per liter of sample) Enterococcus durans |
| --- | --- |
| T POS Enterococcus durans BSL2 (positive control) | 1.03E+06 |
| BEZ_01-10-2021 | 1.16E+04 |
| AGD_04-10-2021 | 0.00E+00 |
| Maera-E_04-10-2021 | 7.25E+03 |
| Z30_05-10-2021 | 2.77E+05 |

These results demonstrate that we can quantify *Enterococcus durans* in wastewater of different sites for a 24 h period (Beziers, Agde, Maera and Z30) and demonstrate differences between the sites of sampling, with the present invention, for adapted measures of prevention and/or treatment.

TABLE 8

| | Number of copies detected (per liter of sample) Candida albicans |
| --- | --- |
| CHU-S-05.08.2020 | 1.46E+05 |
| CHU-S-16.09.2020 | 1.67E+04 |
| CHU-S-30.11.2021 | 8.37E+03 |
| CHU-N-07.12.21 | 0.00E+00 |

These results demonstrate that we can quantify *Candida albicans* in wastewater of different sites for a 24 h period (CHU Sud and CHU North) and demonstrate differences between the sites of sampling, with the present invention, for adapted measures of prevention and/or treatment.

All these results show clearly that the present invention enabled the quantification of different microorganisms in wastewater samples.

The invention claimed is:

1. A method of detecting a pathogen in an environmental liquid matrix, comprising:
   a) taking a sample of the environmental liquid matrix,
   b) extracting nucleic acid without prior purification of the sample, notably without prior clarification of the sample, and
   c) amplifying at least 2 pathogen sequences in a multiplex digital PCR (dPCR) reaction using the nucleic acid of step b) as a template.

2. The method of claim 1, wherein the environmental liquid matrix is selected in the group consisting of: ground water, precipitation (rain or snow), surface water (lakes, ponds, river, runoff, etc.), ice or glacial melt, saline water, estuarian water and brines, waste water (domestic, landfill leachates, mine runoff, etc.), industrial process water and drinking water.

3. The method of claim 1, comprising a further step of concentrating the sample by contacting the sample with a centrifugal filter, wherein this further step takes place after step a).

4. The method of claim 3, comprising centrifuging the sample contacted with the centrifugal filter and recovering the supernatant, wherein the supernatant volume is less than 2 mL.

5. The method of claim 3, wherein the centrifugal filter is contacted with water prior to contacting the centrifugal filter with the sample, wherein the water is preferably at a temperature comprised between 60° C. and 80° C.

6. The method of claim 3, wherein molecules having a molecular weight below 10 kDa are separated from the sample by the further step.

7. The method of claim 1, wherein the sample is homogenised before the RNA extraction.

8. The method of claim 1, wherein the pathogen is
   a bacteria selected from the group consisting of *Salmonella* spp., *Y. pestis, Y. pseudotuberculosis, Y. enterocolitica, Listeria monocytogenes, Taylorella equigenitalis, Mycoplasma gallisepticum, Mycoplasma synoviae, Trichinella* spp., *Toxoplasma gondii, Escherichia coli, Streptococcus uberis, Staphylococcus aureus, L. pneumophila*; or
   a virus selected from the group consisting of adenoviruses, astroviruses, hepatitis A and E viruses, rotavirus, norovirus, coxsackieviruses, polioviruses, polyomaviruses, cytomegalovirus, influenza viruses, coronaviruses, porcine epidemic diarrhoea virus, SARS-CoV-1, SARS-CoV-2, MERS Cov, Paramyxoviridae, bluetongue virus (BTV), bovine viral diarrhoea virus (BVDV), Schmallenberg virus, classical swine fever virus (CSFV), Betaarterivirus suid 1, and African Swine Fever Virus; or
   a fungus selected from the group consisting of *Candida albicans, Cryptococcus neoformans, Aspergillus fumigatus, Aspergillus niger, Trichophyton* spp, *Fusarium, Scedosporium, Alternaria, Exophiala, Histoplasma, Coccidioides*, and *Penicillium marneffei*; or
   mixtures thereof.

9. The method of claim 1, wherein the virus is SARS-CoV-2.

10. The method of claim 1, wherein the multiplex dPCR reaction comprises using at least one probe selected in the group consisting of:

```
                                              (SEQ ID NO. 1)
        ACCCCGCATTACGTTTGGTGGACC, (SEQ ID NO. 2)
        ACAATTTGCCCCCAGCGCTTCAG, and
                                              (SEQ ID NO. 3)
        ACACTAGCCATCCTTACTGCGCTTCG.
```

11. The method of claim 1, wherein the multiplex dPCR reaction comprises using at least one, at least two, at least three, at least four, at least five, or at least six primers selected in the group consisting of:

```
                                              (SEQ ID NO. 4)
        GACCCCAAAATCAGCGAAAT, (SEQ ID NO. 5)
        TCTGGTTACTGCCAGTTGAATCTG, (SEQ ID NO. 6)
        TTACAAACATTGGCCGCAAA,
```

-continued

```
                              (SEQ ID NO. 7)
GCGCGACATTCCGAAGAA, (SEQ ID NO. 8)
ACAGGTACGTTAATAGTTAATAGCGT, and
                              (SEQ ID NO. 9)
ATATTGCAGCAGTACGCACACA.
```

12. The method of claim 1, wherein the multiplex dPCR reaction comprises further using at least one probe of sequence: CCTACCGAAGCAAATG (SEQ ID NO. 10).

13. The method of claim 1, wherein the multiplex dPCR reaction comprises using a primer set comprising:

```
                              (SEQ ID NO. 11)
GAGTGGTTTGACCTTAACGTTTGA, and
                              (SEQ ID NO. 12)
TTGTCGGTTGCAATGCAAGT.
```

14. The method of claim 11, comprising a further step of quantifying the amount of a SARs-CoV-2 nucleic acid comprising the sequence amplified with the primers in the sample of the environmental liquid matrix based on the amplification of step c).

15. The method of claim 13, comprising a further step of quantifying the amount of a nucleic acid comprising the sequence amplified with the primers in the sample of the environmental liquid matrix based on the amplification of step c).

16. The method of claim 15, comprising a further step of normalising an amount of a SARs-CoV-2 nucleic acid comprising the sequence amplified with at least one, at least two, at least three, at least four, at least five, or at least six primers selected in the group consisting of:

```
                              (SEQ ID NO. 4)
GACCCCAAAATCAGCGAAAT, (SEQ ID NO. 5)
TCTGGTTACTGCCAGTTGAATCTG, (SEQ ID NO. 6)
TTACAAACATTGGCCGCAAA, (SEQ ID NO. 7)
GCGCGACATTCCGAAGAA, (SEQ ID NO. 8)
ACAGGTACGTTAATAGTTAATAGCGT, and
                              (SEQ ID NO. 9)
ATATTGCAGCAGTACGCACACA
``` to the amount of nucleic acid comprising the sequence amplified with the primer set comprising:

```
                              (SEQ ID NO. 11)
GAGTGGTTTGACCTTAACGTTTGA, and
                              (SEQ ID NO. 12)
TTGTCGGTTGCAATGCAAGT.
```

17. A method for detecting a SARS-CoV-2 infection in a population comprising detecting SARS-CoV-2 in wastewater according to the method of claim 1.

18. The method of claim 8, wherein the pathogen is an influenza A virus of human, avian, or swine origin.

19. The method of claim 8, wherein the pathogen is a Paramyxoviridae with Morbillivirus genus.

\* \* \* \* \*